(12) United States Patent
Arora et al.

(10) Patent No.: US 9,605,026 B2
(45) Date of Patent: Mar. 28, 2017

(54) HYDROGEN-BOND SURROGATE PEPTIDES AND PEPTIDOMIMETICS FOR P53 REACTIVATION

(71) Applicants: New York University, New York, NY (US); The Ohio State University Research Foundation, Columbus, OH (US); The Regents of the University of Michigan, Ann Arbor, MI (US)

(72) Inventors: Paramjit S. Arora, Cold Spring Harbor, NY (US); Quintin Pan, Dublin, OH (US); Anna Mapp, Ann Arbor, MI (US)

(73) Assignees: NEW YORK UNIVERSITY, New York, NY (US); THE OHIO STATE UNIVERSITY RESEARCH FOUNDATION, Columbus, OH (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/160,001

(22) Filed: Jan. 21, 2014

(65) Prior Publication Data
US 2014/0220159 A1 Aug. 7, 2014

Related U.S. Application Data

(60) Provisional application No. 61/754,574, filed on Jan. 19, 2013, provisional application No. 61/874,190, filed on Sep. 5, 2013.

(51) Int. Cl.
| | |
|---|---|
| *A61K 38/08* | (2006.01) |
| *C07K 7/64* | (2006.01) |
| *C07K 7/56* | (2006.01) |
| *A61K 33/24* | (2006.01) |
| *A61K 45/06* | (2006.01) |
| *A61K 38/00* | (2006.01) |

(52) U.S. Cl.
CPC ......... *C07K 7/64* (2013.01); *A61K 33/24* (2013.01); *A61K 38/08* (2013.01); *A61K 45/06* (2013.01); *C07K 7/56* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,986,881 B1 | 1/2006 | Livingston et al. | |
| 7,202,332 B2 * | 4/2007 | Arora et al. | 530/333 |
| 7,705,118 B2 * | 4/2010 | Arora et al. | 530/317 |
| 8,071,541 B2 * | 12/2011 | Arora et al. | 514/2.9 |
| 2004/0048242 A1 | 3/2004 | La Thangue et al. | |
| 2006/0014675 A1 | 1/2006 | Arora et al. | |
| 2007/0043052 A1 | 2/2007 | Moon et al. | |
| 2010/0234563 A1 | 9/2010 | Arora et al. | |
| 2011/0245175 A1 * | 10/2011 | Arora et al. | 514/13.3 |
| 2012/0172311 A1 | 7/2012 | Nash et al. | |
| 2013/0123196 A1 * | 5/2013 | Arora et al. | 514/21.1 |
| 2013/0210144 A1 * | 8/2013 | Arora et al. | 435/375 |
| 2014/0045769 A1 * | 2/2014 | Arora et al. | 514/19.3 |
| 2014/0205681 A1 * | 7/2014 | Arora et al. | 424/649 |
| 2014/0256615 A1 * | 9/2014 | Blackwell et al. | C07K 5/12 514/2.7 |

FOREIGN PATENT DOCUMENTS

| | | |
|---|---|---|
| JP | 2005/526515 A | 9/2005 |
| JP | 2008/096423 A | 4/2008 |
| WO | 03/100438 A1 | 12/2003 |
| WO | 2005044839 A2 | 5/2005 |
| WO | 2005/118620 A2 | 12/2005 |
| WO | 2009110952 A2 | 9/2009 |
| WO | 2010/033879 A2 | 3/2010 |
| WO | 2010/034028 A1 | 3/2010 |
| WO | WO 2010033879 A2 * | 3/2010 |
| WO | 2012/013979 A1 | 2/2012 |
| WO | 2012122059 A1 | 9/2012 |

OTHER PUBLICATIONS

Harrison, Charlotte; "Reactivating p53." Nat. Rev. Drug Discov. (2012) 11 p. 517.*
Henchey, Laura K. et al, "Inhibition of hypoxia inducible factor 1-transcription coactivator interaction by a hydrogen bond surrogate alpha helix." J. Am. Chem. Soc. (2010) 132 p. 941-942.*
Blackwell, Hellen E. et al, "Ring closing metathesis of olefinic peptides: design, synthesis, and structural characterization of macrocyclic helical peptides." J. Org. Chem. (2001) 66 p. 5291-5302.*
Robinson, Andrea J. et al, "Microwave assisted rcm for the synthesis of carbocyclic peptides." J. Pept. Sci. (2007) 13 p. 280-285).*
Sun, Haiying et al, "Design of small-molecule peptidic and nonpeptidic smac mimetics." Accounts. Chem. Res. (2008) 41(10 p. 1264-1277.*
Grieco, Paolo et al, "Novel alpha-msh peptide analogues with broad spectrum antimicrobial activity." PLoS ONE (2013) 8(4) e61614.*
Avantaggiati, "Meeting Report: Molecular Horizons of Cancer Therapeutics, 11th Pezcoller Symposium," Biochem. Biophys. Acta 1470:R49-R59 (2000).
Chapman & Arora, "Optimized Synthesis of Hydrogen-Bond Surrogate Helices: Surprising Effects of Microwave Heating on the Activity of Grubbs Catalysts," Org. Lett. 8(25):5825, S1-S17 (Supporting Information) (2006).
Chapman & Arora, "Optimized Synthesis of Hydrogen-Bond Surrogate Helices: Surprising Effects of Microwave Heating on the Activity of Grubbs Catalysts," Org. Lett. 8(25):5825-28 (2006) (pub'd online Nov. 15, 2006).
Chapman et al., "A Highly Stable Short α-Helix Constrained by a Main-Chain Hydrogen-Bond Surrogate," J. Am. Chem. Soc'y 126:12252-53 (2004).
Dames et al., "Structural Basis for Hif-1α/CBP Recognition in the Cellular Hypoxic Response," Proc. Nat'l Acad. Sci. 99(8):5271-76 (2002).

(Continued)

*Primary Examiner* — Fred Reynolds
(74) *Attorney, Agent, or Firm* — LeClairRyan, a Professional Corporation

(57) ABSTRACT

The present invention relates to peptidomimetics for reactivating p53. Methods of using the peptidomimetics are also disclosed.

12 Claims, 7 Drawing Sheets

(56) References Cited

OTHER PUBLICATIONS

Dimartino et al., "Solid-Phase Synthesis of Hydrogen-Bond Surrogate-Derived α-Helices," Org. Lett. 7(12):2389-92 (2005).
Elkins et al., "Structure of Factor-Inhibiting Hypoxia-Inducible Factor (HIF) Reveals Mechanism of Oxidative Modification of HIF-1α," J. Biol. Chem. 278(3):1802-06 (2003).
EP 09815315.8, European Search Report and Opinion (Feb. 9, 2012).
Freedman et al., "Structural Basis for Recruitment of CBP/p300 by Hypoxia-Inducible Factor-1α," Proc. Nat'l Acad. Sci. 99(8):5367-72 (2002).
Henchey et al., "Contemporary Strategies for the Stabilization of Peptides in the α-Helical Conformation," Curr. Opin. Chem. Biol. 12(6):692-97 (2008).
Henchey et al., "Inhibition of Hypoxia Inducible Factor 1—Transcription Coactivator Interaction by a Hydrogen Bond Surrogate α-Helix," J. Am. Chem. Soc'y 132:941-43 (2010) (pub'd online Dec. 30, 2009).
Hirota & Semenza, "Regulation of Angiogenesis by Hypoxia-Inducible Factor 1," Crit. Rev. Oncol./Hematol. 59:15-26 (2006).
Kung et al., "Suppression of Tumor Growth Through Disruption of Hypoxia-Inducible Transcription," Nat. Med. 6(12):1335-40 (2000).
Min et al., "Structure of an HIF-1α—pVHL Complex: Hydroxyproline Recognition in Signaling," Science 296:1886-89 (2002).
PCT/US2009/057592, International Preliminary Report on Patentability (Mar. 22, 2011).
PCT/US2009/057592, International Search Report (May 18, 2010).
PCT/US2009/057592, Written Opinion (May 18, 2010).
Protein Databank No. 1L3E_A (Jul. 17, 2008).
Semenza, "Targeting HIF-1 for Cancer Therapy," Nat. Rev. Cancer 3:721-32 (2003).
Wang et al., "Enhanced Metabolic Stability and Protein-Binding Properties of Artificial α Helices Derived from a Hydrogen-Bond Surrogate: Application to Bcl-xl," Agnew. Chem. Int'l Ed. 44:6525-29 (2005).
Wang et al., "Evaluation of Biologically Relevant Short α-Helices Stabilized by a Main-Chain Hydrogen-Bond Surrogate," J. Am. Chem. Soc'y 128:9248-56 (2006).
Wang et al., "Nucleation and Stability of Hydrogen-Bond Surrogate-Based α-Helices," Org. Biomol. Chem. 4(22):4074-81 (2006).
Xie et al., "Targeting HPV16 E6-p300 Interaction Reactivates p53 and Inhibits the Tumorigenicity of HPV-Positive Head and Neck Squamous Cell Carcinoma," Oncogene 33:1037-46 (2014) (pub'd online Mar. 11, 2013).
International Preliminary Report on Patentability and Written Opinion for corresponding PCT/US2014/012331 (Jul. 21, 2015), May 21, 2014.
International Search Report for corresponding PCT/US2014/012331 (May 21, 2014).
Wang et al., "c-Jun Triggers Apoptosis in Human Vascular Endothelial Cells," Circ. Res. 85: 387-393 (1999).
Albrecht et al., "Easy and Fast Detection and Genotyping of High-Risk Human Papillomavirus by Dedicated DNA Microarrays," J. Virol. Methods 137:236-44 (2006).
Allen, "Long-Circulating (Sterically Stabilized) Liposomes for Targeted Drug Delivery," Trends Pharmacol. Sci. 15:215-20 (1994).
Almeida & Souto, "Solid Lipid Nanoparticles as a Drug Delivery System for Peptides and Proteins," Adv. Drug Deliv. Rev. 59:478-90 (2007).
Ausubel et al., "Complementary Mutations in an Antigenic Peptide Allow for Crossreactivity of Autoreactive T-Cell Clones," Proc. Natl. Acad. Sci. USA 93:15317-22 (1996).
Candelaria et al., "Radiosensitizers in Cervical Cancer. Cisplatin and Beyond," Radiation Oncol. 1(15):1-17 (2006).
HeLa (ATCC® CCL-2TH), http://www.atcc.org/Products/All/CCL-2.aspx, (last accessed Feb. 18, 2015).
Kulkarni et al., "Promotion of Selective Cell Attachment by the RGD Sequence in Dentine Matrix Protein 1," Arch. Oral Biol. 45:475-84 (2000).
Mandell & Kortemme, "Computer-Aided Design of Functional Protein Interactions," Nat. Chem. Biol. 5(11):797-807 (2009).
Marshall et al., "Factors Governing Helical Preference of Peptides Containing Multiple α,α-Dialkyl Amino Acids," Proc. Nat. Acad. Sci. USA 87:487-91 (1990).
Protein Data Bank Accession No. 1H2K,"Sequence" tab, http://www.rcsb.org/explore.do?structured=1h2k (last accessed Feb. 20, 2014).
Sharma & Sharma, REVIEW, "Liposomes in Drug Delivery: Progress and Limitations," Int'l J. Pharmaceut. 154:123-40 (1997).
Takeuchi et al., "Mucoadhesive Nanoparticulate Systems for Peptide Drug Delivery" Adv. Drug Deliv. Rev. 47:39-54 (2001).
Wender et al., "The Design, Synthesis, and Evaluation of Molecules That Enable or Enhance Cellular Uptake: Peptoid Molecular Transporters," Proc. Nat'l Acad. Sci. 97(24):13003-08 (2000).
Yang et al., "Predominant Suppression of Apoptosome by Inhibition of Apoptosis Protein in Non-Small Cell Lung Cancer H460 Cells: Therapeutic Effect of a Novel Polyarginine-Conjugated Smac Peptide," Canc. Res. 63:831-37(2003).
Yin, "Constrained Peptides as Miniature Protein Structures," ISRN Biochem., Article ID 692190, pp. 1-15 (2012).
Extended European Search Report for corresponding European Patent Application No. 14740418.0 (Aug. 19, 2016).

* cited by examiner

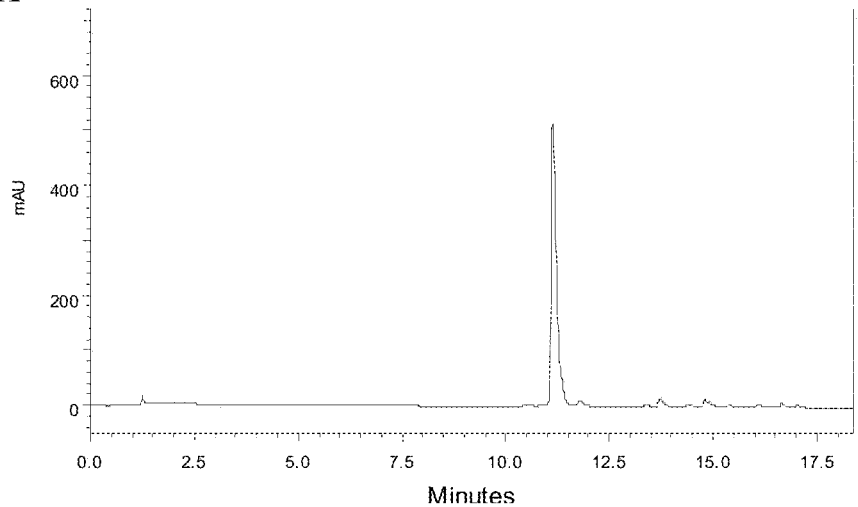
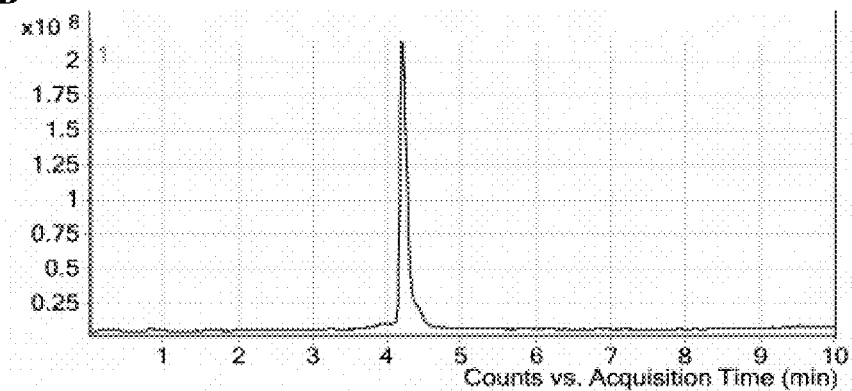
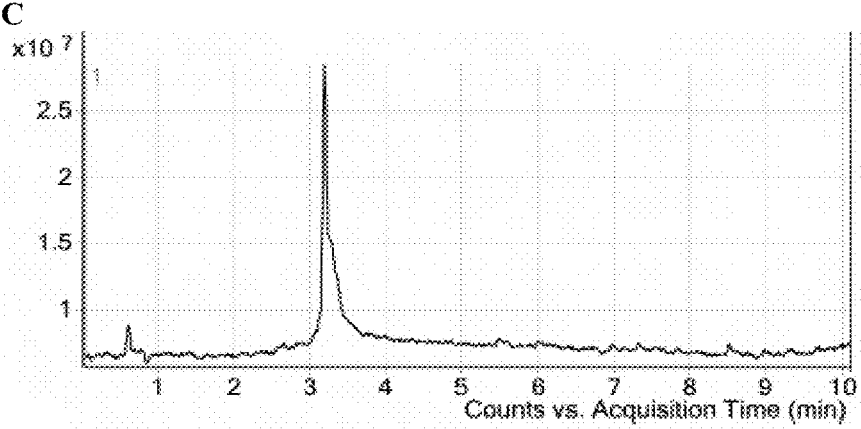
Figures 1A–C

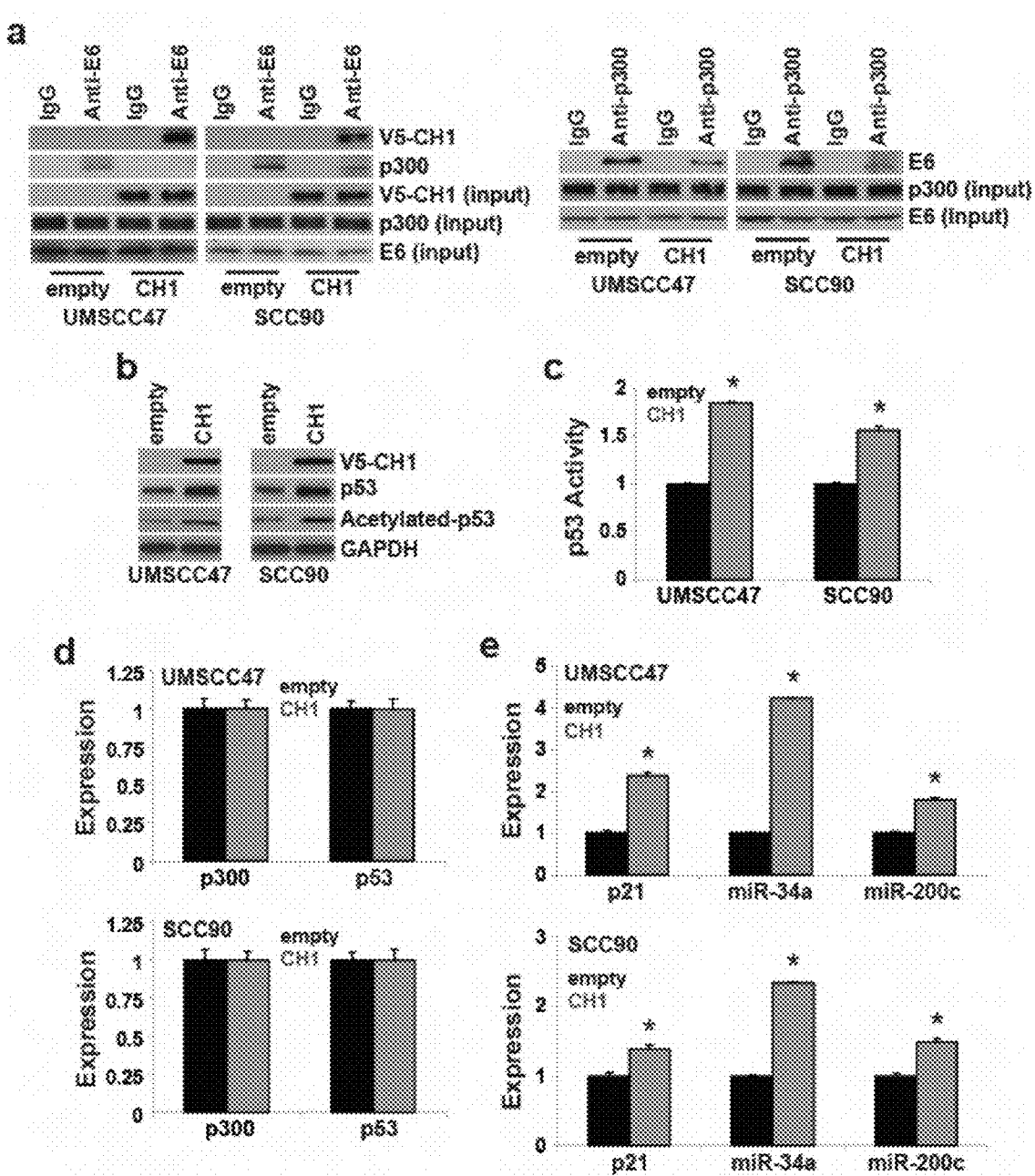
Figures 2A–E

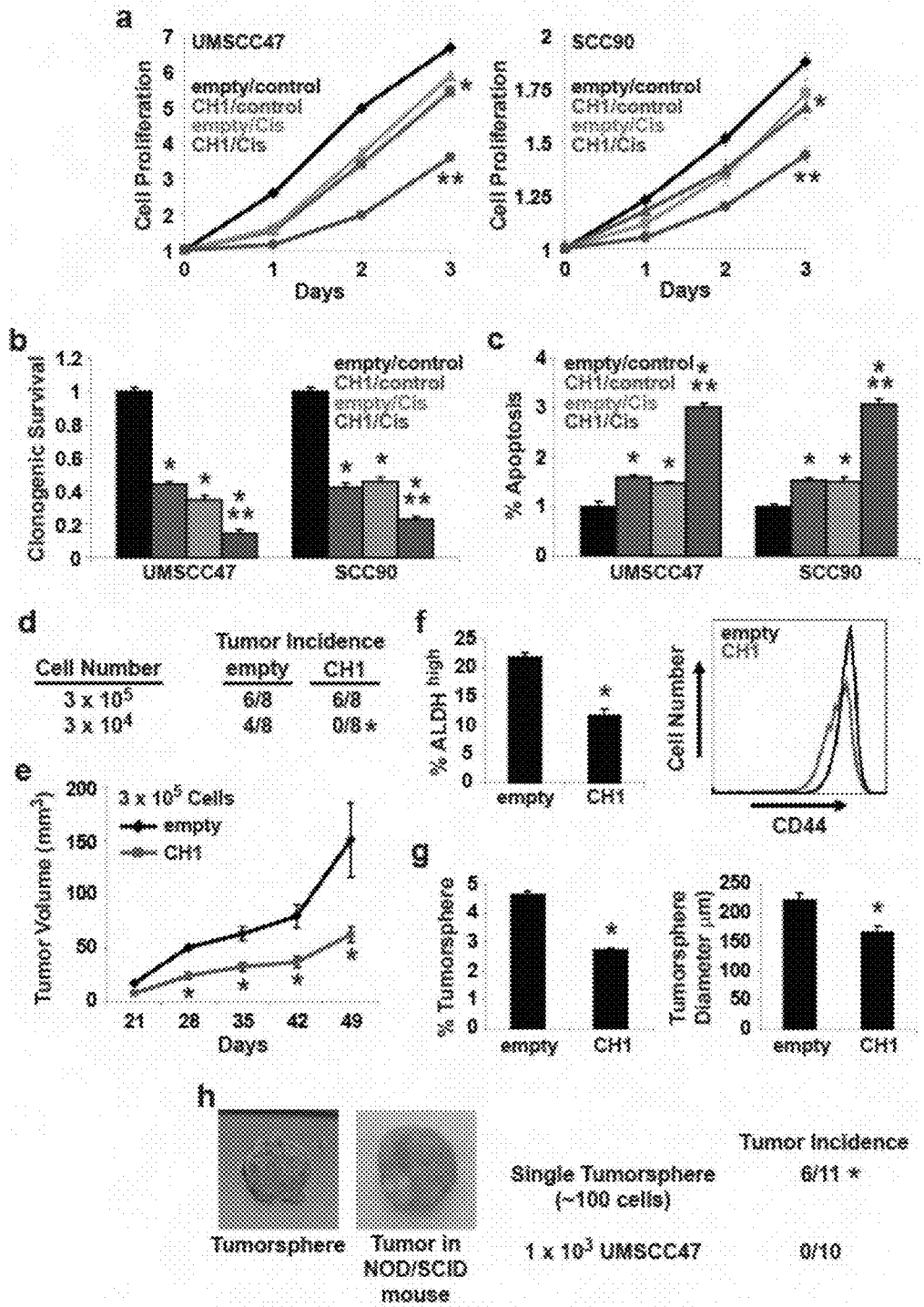
Figures 3A–H

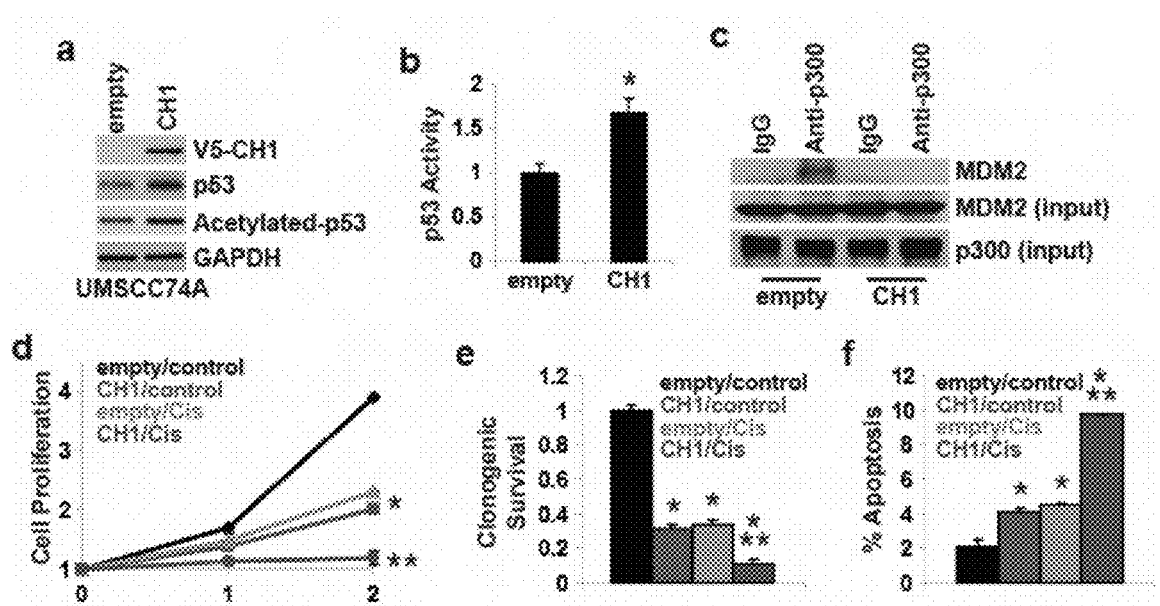
Figures 4A–F

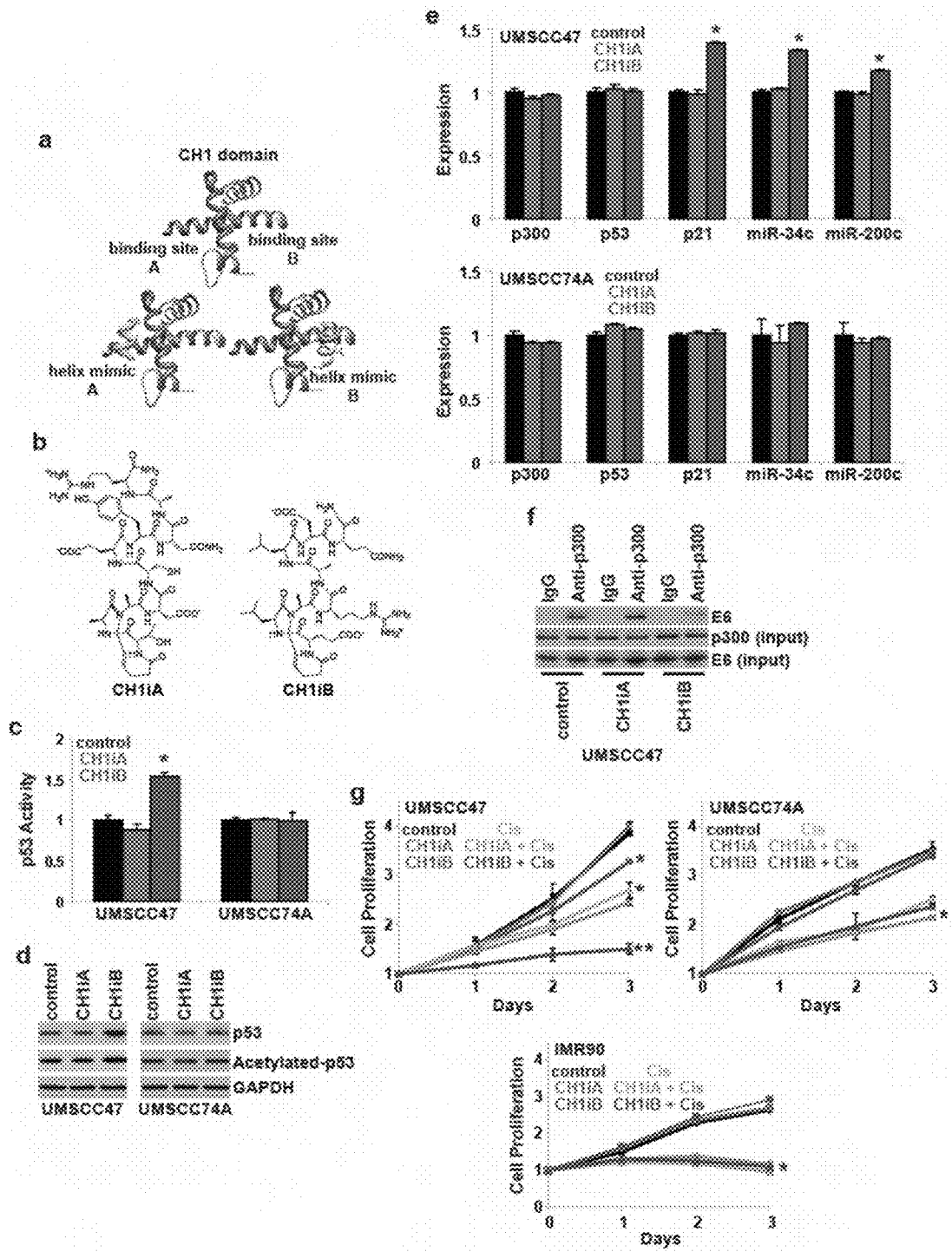
Figures 5A–G

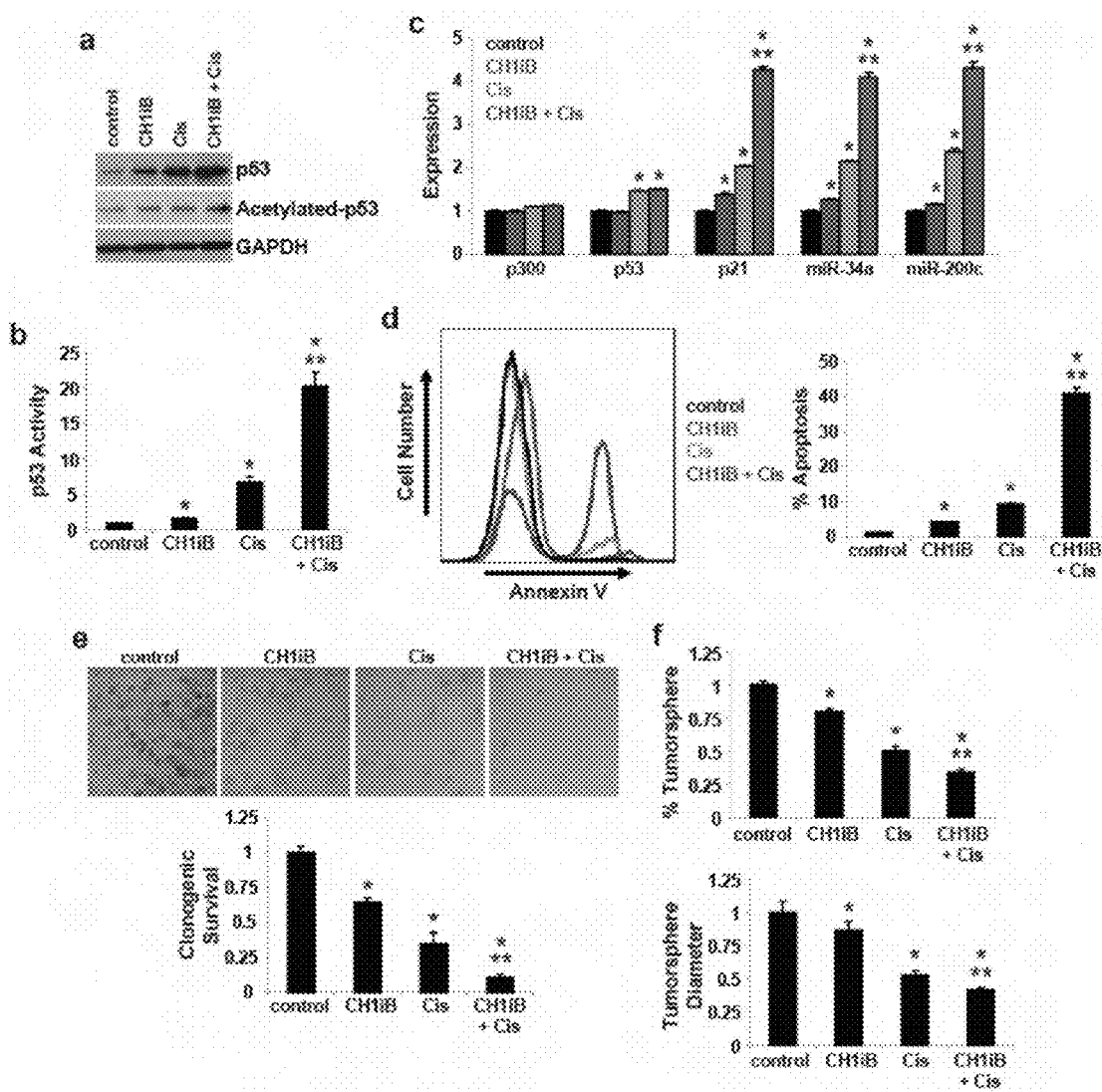
Figures 6A–F

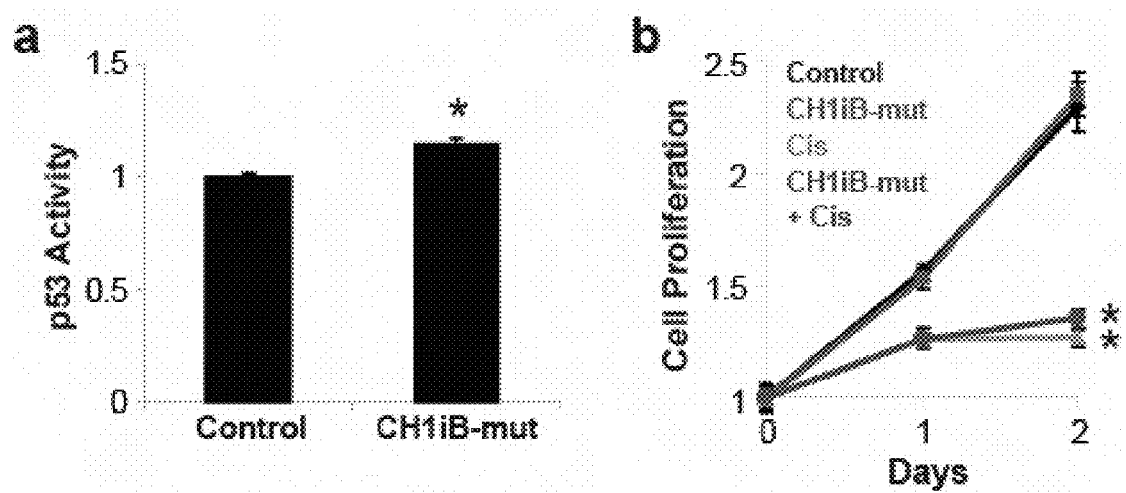
Figures 7A–B

```
                        SEQUENCE LISTING

<160> NUMBER OF SEQ ID NOS: 9

<210> SEQ ID NO 1
    <211> LENGTH: 29
    <212> TYPE: PRT
    <213> ORGANISM: Artificial
    <220> FEATURE:
    <223> OTHER INFORMATION: Signal peptide

<400> SEQUENCE: 1

Met Met Ser Phe Val Ser Leu Leu Leu Val Gly Ile Leu Phe Tyr Ala
    1               5                   10                  15

Thr Glu Ala Glu Gln Leu Thr Lys Cys Glu Val Phe Gln
                20                  25

<210> SEQ ID NO 2
    <211> LENGTH: 4
    <212> TYPE: PRT
    <213> ORGANISM: Artificial
    <220> FEATURE:
    <223> OTHER INFORMATION: Retention signal

<400> SEQUENCE: 2

Lys Glu Asp Leu
    1

<210> SEQ ID NO 3
    <211> LENGTH: 8
    <212> TYPE: PRT
    <213> ORGANISM: Artificial
    <220> FEATURE:
    <223> OTHER INFORMATION: Nuclear transport peptide

<400> SEQUENCE: 3

Pro Pro Lys Lys Lys Arg Lys Val
    1               5
```

```
<210> SEQ ID NO 4
<211> LENGTH: 25
<212> TYPE: PRT
<213> ORGANISM: Artificial
<220> FEATURE:
<223> OTHER INFORMATION: Transport peptide

<400> SEQUENCE: 4

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 5
<211> LENGTH: 34
<212> TYPE: DNA
<213> ORGANISM: Artificial
<220> FEATURE:
<223> OTHER INFORMATION: Forward primer

<400> SEQUENCE: 5
ggatccatgc cagagaagcg caagctcatc cagc                              34

<210> SEQ ID NO 6
<211> LENGTH: 34
<212> TYPE: DNA
<213> ORGANISM: Artificial
<220> FEATURE:
<223> OTHER INFORMATION: Reverse primer

<400> SEQUENCE: 6
ctcgagatca ccagcatttt tgaggggggag acac                             34

<210> SEQ ID NO 7
<211> LENGTH: 10
<212> TYPE: PRT
<213> ORGANISM: Artificial
<220> FEATURE:
<223> OTHER INFORMATION: CH1iA
<220> FEATURE:
<221> NAME/KEY: MISC_FEATURE
<222> LOCATION: (3)..(3)
<223> OTHER INFORMATION: Xaa at position3 is N-allylalanine

<400> SEQUENCE: 7

Thr Ala Xaa Asp Cys Glu Tyr Asn Ala Arg
1               5                   10

<210> SEQ ID NO 8
<211> LENGTH: 8
<212> TYPE: PRT
<213> ORGANISM: Artificial
<220> FEATURE:
<223> OTHER INFORMATION: CH1iB
<220> FEATURE:
<221> NAME/KEY: MISC_FEATURE
<222> LOCATION: (3)..(3)
<223> OTHER INFORMATION: Xaa at position 3 is N-allylalanine

<400> SEQUENCE: 8

Glu Leu Xaa Arg Ala Leu Asp Gln
1               5

<210> SEQ ID NO 9
<211> LENGTH: 8
<212> TYPE: PRT
<213> ORGANISM: Artificial
<220> FEATURE:
```

```
<223> OTHER INFORMATION: CH1iB-MUT
<220> FEATURE:
<221> NAME/KEY: MISC_FEATURE
<222> LOCATION: (3)..(3)
<223> OTHER INFORMATION: Xaa at position 3 is N-allylalanine

<400> SEQUENCE: 9

Glu Leu Xaa Arg Ala Ala Asp Gln
1               5
```

HYDROGEN-BOND SURROGATE PEPTIDES AND PEPTIDOMIMETICS FOR P53 REACTIVATION

This application claims the priority benefit of U.S. Provisional Patent Application Ser. No. 61/754,574, filed Jan. 19, 2013, and U.S. Provisional Patent Application Ser. No. 61/874,190, filed Sep. 5, 2013, each of which is hereby incorporated by reference in its entirety.

This invention was made with government support under grant numbers R01CA135096 and R01GM073943 awarded by the National Institutes of Health. The government has certain rights in this invention.

FIELD OF THE INVENTION

This invention is directed generally to artificially constrained peptides and peptidomimetics for targeting the E6-p300 interaction.

BACKGROUND OF THE INVENTION

Human papillomaviruses (HPV) are small, double-stranded DNA viruses that infect the epithelium. More than 100 HPV types have been identified. They are differentiated by the genetic sequence of the outer capsid protein L1. Most HPV types infect the cutaneous epithelium and cause common skin warts. About 40 types infect the mucosal epithelium; these are categorized according to their epidemiologic association with cervical cancer. Infection with low-risk, or nononcogenic types, such as types 6 and 11, can cause benign or low-grade cervical cell abnormalities, genital warts and laryngeal papillomas. High-risk, or oncogenic, HPV types act as carcinogens in the development of cervical cancer and other anogenital cancers. High-risk types (currently including types 16, 18, 31, 33, 35, 39, 45, 51, 52, 56, 58, 59, 68, 69, 73, 82) can cause low-grade cervical cell abnormalities, high-grade cervical cell abnormalities that are precursors to cancer, and anogenital cancers. High-risk HPV types are detected in 99% of cervical cancers. Type 16 is the cause of approximately 50% of cervical cancers worldwide, and types 16 and 18 together account for about 70% of cervical cancers.

Head and neck squamous cell carcinoma (HNSCC) is the sixth most common cancer with approximately 600,000 new cases worldwide (Kamangar et al., "Patterns of Cancer Incidence, Mortality, and Prevalence Across Five Continents: Defining Priorities to Reduce Cancer Disparities in Different Geographic Regions of the World," *J. Clin. Oncol.* 24(14):2137-50 (2006)). HPV infection is recognized as a major risk factor for the development of a subset of HNSCC, oropharyngeal SCC. HPV16 is the most prevalent subtype and accounts for ~90% of HPV-positive HNSCC (Gillison et al., "Evidence for a Causal Association Between Human Papillomavirus and a Subset of Head and Neck Cancers," *J. Nat'l Cancer Inst.* 92(9):709-20 (2000); Klussmann et al., "Expression of p16 Protein Identifies a Distinct Entity of Tonsillar Carcinomas Associated With Human Papillomavirus," *Am. J. Pathol.* 162(3):747-53 (2003)). Epidemiological data indicate that the prevalence of HPV-positive HNSCC has increased by ~3-fold in the past three decades in the United States and Europe (Licitra et al., "Advances in the Changing Patterns of Aetiology of Head and Neck Cancers," *Curr. Opin. Otolaryngol. Head Neck Surg.* 14(2):95-99 (2006); Shiboski et al., "Tongue and Tonsil Carcinoma: Increasing Trends in the U.S. Population Ages 20-44 Years," *Cancer* 103(9): 1843-49 (2005); Sturgis & Cinciripini, "Trends in Head and Neck Cancer Incidence in Relation to Smoking Prevalence: An Emerging Epidemic of Human Papillomavirus-Associated Cancers?" *Cancer* 110(7): 1429-35 (2007)). Data obtained from the Swedish Cancer Registry showed a 2.8-fold increase in the incidence of oropharyngeal SCC in the Stockholm area between 1970 and 2002. Interestingly, over the same time period, the incidence of HPV-positive oropharyngeal SCC increased by ~3-fold from 23% in the 1970s to 68% in the 2000s (Hammarstedt et al., "Human Papillomavirus as a Risk Factor for the Increase in Incidence of Tonsillar Cancer," *Int'l J. Cancer* 119(11): 2620-23 (2006). Based on these alarming numbers, it has been suggested that an epidemic of HPV-positive HNSCC will emerge in the near future (Sturgis & Cinciripini, "Trends in Head and Neck Cancer Incidence in Relation to Smoking Prevalence: An Emerging Epidemic of Human Papillomavirus-Associated Cancers?" Cancer 110(7): 1429-35 (2007); Hammarstedt et al., "Human Papillomavirus as a Risk Factor for the Increase in Incidence of Tonsillar Cancer," *Int'l J. Cancer* 119(11):2620-23 (2006)).

There is concrete clinical data that the HPV vaccine, Gardasil, protects against HPV-positive cervical, vaginal, and vulvar carcinomas (Group FIS, "Quadrivalent Vaccine Against Human Papillomavirus to Prevent High-Grade Cervical Lesions," *N. Engl. J. Med.* 356(19):1915-27 (2007)). It is assumed that the HPV vaccine will protect against HPV-positive HNSCC; however, there is no clinical evidence to support this expectation. The HPV vaccine uptake in females has been modest even though the Centers for Disease Control and Prevention issued a recommendation to vaccinate females, between the ages of 9 to 26, for high-risk HPV in 2006. A study using the 2010 National Health Interview Survey showed that only about 30% and 15% of eligible females received one dose and the full three-dose series of the HPV vaccine, respectively (Laz et al., "An Update on Human Papillomavirus Vaccine Uptake Among 11-17 Year Old Girls in the United States: National Health Interview Survey, 2010," *Vaccine* 30(24):3534-40 (2012)). Gardasil was approved for males, 9 to 26 years old, in 2009; however, vaccine uptake was reported to be extremely poor at 2% (Reiter et al., "HPV Vaccine and Adolescent Males," *Vaccine* 29(34):5595-602 (2012)). It is clear that a significant number of age eligible females and males are not vaccinated and may remain unprotected against HPV-positive carcinomas, including HNSCC, over their lifetime. Gardasil was shown to be highly effective to protect against cervical carcinoma for HPV-infection naïve individuals but provided much more limited benefit to individuals already exposed to high-risk HPV, including HPV16 (Munoz et al., "Impact of Human Papillomavirus (HPV)-6/11/16/18 Vaccine on All HPV-Associated Genital Diseases in Young Women," *J. Nat'l Cancer Inst.* 102(5):325-39 (2010); Sigurdsson et al., "The Efficacy of HPV 16/18 Vaccines on Sexually Active 18-23 Year Old Women and the Impact of HPV Vaccination on Organized Cervical Cancer Screening," *Acta Obstet. Gynecol. Scand.* 88(1):27-35 (2009)). HPV vaccination is not recommended for adults >26 years old since these individuals are likely to be exposed to high-risk HPV already. Therefore, several generations of individuals already exposed to high-risk HPV or are >26 years old will not be vaccinated routinely or even if vaccinated will have minimal protection against HPV-positive carcinomas, including HNSCC. In light of these points, there is a clinical need to develop alternative therapeutic strategies to manage an anticipated growing number of HPV-positive HNSCC patients.

In contrast to HPV-negative HNSCC, p53 is predominantly wildtype in HPV-positive HNSCC (Balz et al., "Is the p53 Inactivation Frequency in Squamous Cell Carcinomas of the Head and Neck Underestimated?Analysis of p53 Exons 2-11 and Human Papillomavirus 16/18 E6 Transcripts in 123 Unselected Tumor Specimens," *Cancer Res.* 63(6): 1188-91 (2003); Agrawal et al., "Exome Sequencing of Head and Neck Squamous Cell Carcinoma Reveals Inactivating Mutations in NOTCH1," *Science* 333(6046): 1154-57 (2011); Stransky et al., "The Mutational Landscape of Head and Neck Squamous Cell Carcinoma," *Science* 333 (6046): 1157-60 (2011)). However, high-risk HPV E6 inactivates p53 through two distinct mechanisms. E6 associates with E6AP to degrade p53 through the proteasome pathway and associates with p300 to block p300-mediated p53 acetylation (Huibregtse et al., "A Cellular Protein Mediates Association of p53 With the E6 Oncoprotein of Human Papillomavirus Types 16 or 18," *EMBO J.* (13):4129-35 (1991); Scheffner et al., "The HPV-16 E6 and E6-AP Complex Functions as a Ubiquitin-Protein Ligase in the Ubiquitination of p53," *Cell* 75(3):495-505 (1993); Talis et al., "The Role of E6AP in the Regulation of p53 Protein Levels in Human Papillomavirus (HPV)-Positive and HPV-Negative Cells," *J. Biol. Chem.* 273(11):6439-45 (1998); Zimmermann et al., "The Human Papillomavirus Type 16 E6 Oncoprotein Can Down-Regulate p53 Activity by Targeting the Transcriptional Coactivator CBP/p300," *J. Virol.* 73(8):6209-19 (1999); Patel et al., "The E6 Protein of Human Papillomavirus Type 16 Binds to and Inhibits Co-Activation by CBP and p300," *EMBO J.* 18(18):5061-72 (1999); Thomas & Chiang, "E6 Oncoprotein Represses p53-Dependent Gene Activation Via Inhibition of Protein Acetylation Independently of Inducing p53 Degradation," *Mol. Cell* 17(2):251-64 (2005)). Acetylation of p53 enhances p53 stability, and transcriptional activity (Zimmermann et al., "The Human Papillomavirus Type 16 E6 Oncoprotein Can Down-Regulate p53 Activity by Targeting the Transcriptional Coactivator CBP/p300," *J. Virol.* 73(8): 6209-19 (1999); Patel et al., "The E6 Protein of Human Papillomavirus Type 16 Binds to and Inhibits Co-Activation by CBP and p300," *EMBO J.* 18(18):5061-72 (1999); Thomas & Chiang, "E6 Oncoprotein Represses p53-Dependent Gene Activation Via Inhibition of Protein Acetylation Independently of Inducing p53 Degradation," *Mol. Cell* 17(2):251-64 (2005); Ito et al., "MDM2-HDAC1-Mediated Deacetylation of p53 Is Required for Its Degradation," *EMBO J.* 21(22):6236-45 (2002); Li et al., "Acetylation of p53 Inhibits Its Ubiquitination by Mdm2," *J. Biol. Chem.* 277(52):50607-11 (2002)). Inactivation of p53 by E6 is indispensible for HPV-mediated tumorigenesis suggesting that reactivation of p53 may be a strategy to ablate HPV-positive carcinoma cells. Several genetic and chemical strategies to reactivate p53 have been demonstrated in HPV-positive cervical carcinomas. Most of these approaches focused on targeting E6 levels, E6AP levels, or E6-E6AP association to increase p53 stability and accumulation (Beerheide et al., "Potential Drugs Against Cervical Cancer: Zinc-Ejecting Inhibitors of the Human Papillomavirus Type 16 E6 Oncoprotein," *J. Nat'l Cancer Inst.* 91(14):1211-20 (1999); Beerheide et al., "Inactivation of the Human Papillomavirus-16 E6 Oncoprotein by Organic Disulfides," *Bioorg. Med. Chem.* 8(11):2549-60 (2000); Courtete et al., "Suppression of Cervical Carcinoma Cell Growth by Intracytoplasmic Codelivery of Anti-Oncoprotein E6 Antibody and Small Interfering RNA," *Mol. Cancer. Ther.* 6(6):1728-35 (2007); Beer-Romero et al., "Antisense Targeting of E6AP Elevates p53 in HPV-Infected Cells but Not in Normal Cells," *Oncogene* 14(5):595-602 (1997); Koivusalo et al., "Activation of p53 in Cervical Cancer Cells by Human Papillomavirus E6 RNA Interference Is Transient, but Can Be Sustained by Inhibiting Endogenous Nuclear Export-Dependent p53 Antagonists," *Cancer Res.* 66(24):11817-24 (2006); Zhao et al., "Rescue of p53 Function by Small-Molecule RITA in Cervical Carcinoma by Blocking E6-Mediated Degradation," *Cancer Res.* 70(8):3372-81 (2010).

There is a clinical need to develop alternate therapeutic strategies to manage the growing number of HPV-positive HNSCC patients (and those with other HPV-associated cancers). The present invention is directed to overcoming these and other deficiencies in the art.

SUMMARY OF THE INVENTION

One aspect of the present invention relates to a peptidomimetic, where the peptidomimetic:
(i) mimics a helix having the formula $X_1$-$X_2$-$X_2$-$X_3$-$X_2$-$X_2$-$X_1$-$X_4$, wherein each $X_1$ is any negatively charged residue, each $X_2$ is any hydrophobic residue, $X_3$ is any positively-charged residue, and $X_4$ is any polar residue; and
(ii) is selected from the group consisting of:
(a) a compound of Formula I:

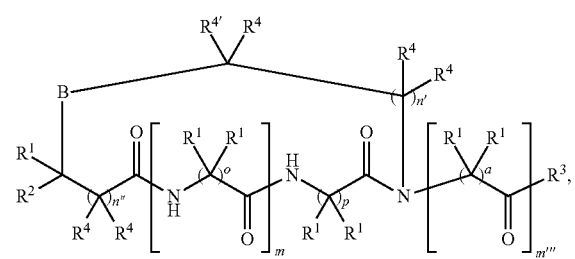

wherein:
B is $C(R^1)_2$, O, S, or $NR^1$;
each $R^1$ is independently hydrogen, an amino acid side chain, an alkyl, an alkenyl, an alkynyl, a cycloalkyl, a heterocyclyl, an aryl, a heteroaryl, or an arylalkyl;
$R^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; $-OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; $-(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

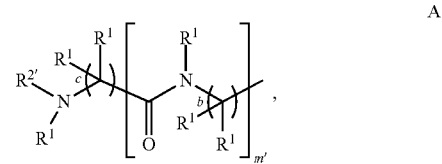

wherein:
R²' is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR⁵ wherein R⁵ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —(CH₂)₀₋₁N(R⁵)₂ wherein each R⁵ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

each R⁴ is independently hydrogen, an alkyl, an alkenyl, an alkynyl, a cycloalkyl, a heterocyclyl, an aryl, a heteroaryl, or an arylalkyl;

R⁴' is hydrogen, an alkyl, an alkenyl, an alkynyl, a cycloalkyl, a heterocyclyl, an aryl, a heteroaryl, an arylalkyl, or a double bond between C(R⁴',R⁴) and B;

a is one or two;

m, n', and n" are each independently zero, one, two, three, or four;

m'" is zero or one;

each o is independently one or two; and p is one or two;

(b) a compound of Formula II:

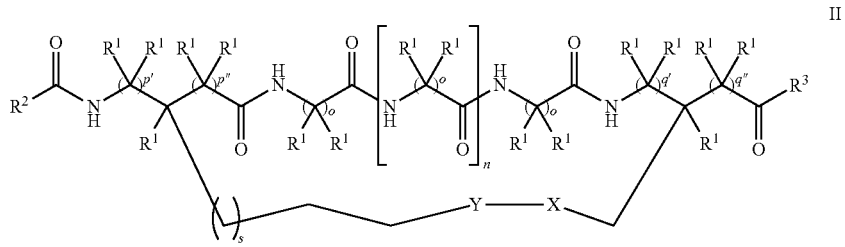

m' is zero or any number;
each b is independently one or two; and
c is one or two;

R³ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR⁵ wherein R⁵ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —N(R⁵)₂ wherein each R⁵ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

wherein:
each R¹ is independently hydrogen, an amino acid side chain, an alkyl, an alkenyl, an alkynyl, a cycloalkyl, a heterocyclyl, an aryl, a heteroaryl, or an arylalkyl;

R² is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR⁵ wherein R⁵ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —(CH₂)₀₋₁N(R⁵)₂ wherein each R⁵ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

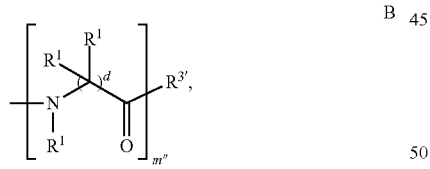

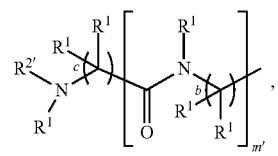

wherein:
R³' is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR⁵ wherein R⁵ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —N(R⁵)₂ wherein each R⁵ is independently hydrogen, an alkyl, an alkenyl, an alkynyl, a cycloalkyl, an aryl, a heteroaryl, an arylalkyl, an acyl, a peptide, a targeting moiety, or a tag;

m" is zero or any number; and
each d is independently one or two;

wherein:
R²' is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR⁵ wherein R⁵ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —(CH₂)₀₋₁N(R⁵)₂ wherein each R⁵ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

m' is zero or any number;

each b is independently one or two; and c is one or two;

$R^3$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

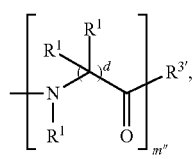

B wherein:

$R^{3'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —$N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

m" is zero or any number; and each d is independently one or two;

n is one or four;

each o is independently one or two;

one of p' and p" is zero and the other is zero or one;

one of q' and q" is zero and the other is zero or one;

s is one, two, three, four, or five; and

Y—X is a hydrocarbon, an amide bond, an alkane, an alkene, an alkyne, a triazole, or a disulfide bond; and (c) a compound of Formula III:

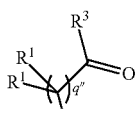

III

-continued

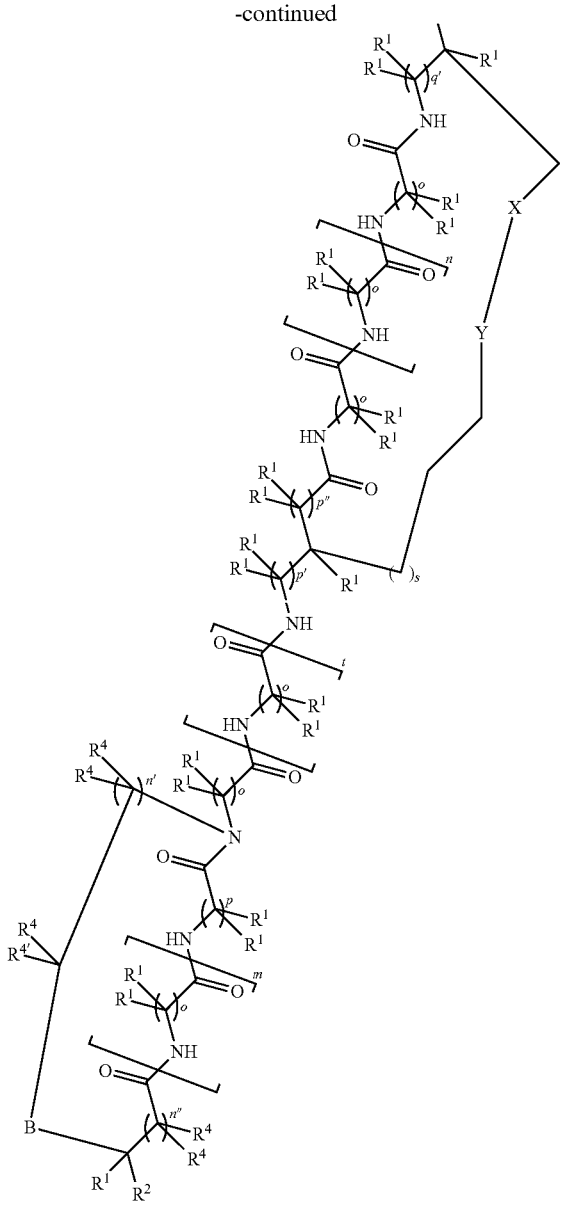

wherein:

B is $C(R^1)_2$, O, S, or $NR^1$;

each $R^1$ is independently hydrogen, an amino acid side chain, an alkyl, an alkenyl, an alkynyl, a cycloalkyl, a heterocyclyl, an aryl, a heteroaryl, or an arylalkyl;

$R^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

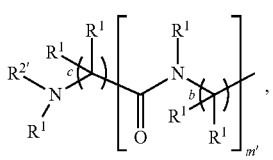

A wherein:
R$^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR$^5$ wherein R$^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —(CH$_2$)$_{0-1}$N(R$^5$)$_2$ wherein each R$^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

m' is zero or any number;
each b is independently one or two; and
c is one or two;

R$^3$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR$^5$ wherein R$^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —N(R$^5$)$_2$ wherein each R$^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

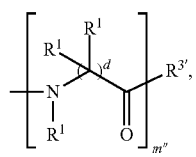

B wherein:
R$^{3'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR$^5$ wherein R$^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —N(R$^5$)$_2$ wherein each R$^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

m" is zero or any number; and
each d is independently one or two;

each R$^4$ is independently hydrogen, an alkyl, an alkenyl, an alkynyl, a cycloalkyl, a heterocyclyl, an aryl, a heteroaryl, or an arylalkyl;

R$^{4'}$ is hydrogen, an alkyl, an alkenyl, an alkynyl, a cycloalkyl, a heterocyclyl, an aryl, a heteroaryl, an arylalkyl, or a double bond between C(R$^{4'}$,R$^4$) and B;

m, n', and n" are each independently zero, one, two, three, or four;

n is one or four;
each o is independently one or two;
p is one or two;
one of p' and p" is zero and the other is zero or one;
one of q' and q" is zero and the other is zero or one;
s is one, two, three, four, or five; and
Y—X is a hydrocarbon, an amide bond, an alkane, an alkene, an alkyne, a triazole, or a disulfide bond.

A second aspect of the present invention relates to a pharmaceutical composition comprising a peptidomimetic of the present invention and a pharmaceutically acceptable vehicle.

A third aspect of the present invention relates to a method of treating or preventing in a subject a disorder mediated by interaction of E6 with CREB-binding protein and/or p300, the method comprising administering to the subject a peptidomimetic of the present invention under conditions effective to treat or prevent the disorder.

A fourth aspect of the present invention relates to a method of inducing apoptosis of a cell, the method comprising contacting the cell with a peptidomimetic of the present invention under conditions effective to induce apoptosis of the cell.

A fifth aspect of the present invention relates to a method of inducing decreasing survival and/or proliferation of a cell, the method comprising contacting the cell with a peptidomimetic of the present invention under conditions effective to decrease survival and/or proliferation of the cell.

A sixth aspect of the present invention relates to a method of preventing or reversing inactivation of p53 in a cell, the method comprising contacting the cell with a peptidomimetic of the present invention under conditions effective to prevent or reverse inactivation of p53 in a cell.

A seventh aspect of the present invention relates to a method of inhibiting p300-mediated acetylation of a transcription factor in a cell, the method comprising contacting the cell with a peptidomimetic of the present invention under conditions effective to inhibit p300-mediated acetylation of the transcription factor in the cell.

In this study, we took a novel approach and functionally reactivated p53 in HPV-positive HNSCC by blocking the interaction between E6 and p300. Ectopic expression of the CH1 domain of p300 squelched E6 to disrupt E6-p300 association resulting in an increase in p53 acetylation, accumulation, and activity. Exogenous CH1 promoted a pleiotropic, anti-cancer effect in HPV-positive HNSCC partly due to a reduction in the cancer initiating cell (CIC) population. A small molecule CH1 domain inhibitor, CH1iB, reactivated p53 and dramatically potentiated the efficacy of cis-platinum in HPV-positive HNSCC. Taken together, our work revealed a novel druggable approach to reactivate p53 in HPV-positive HNSCC that is expected to translate to other HPV-positive carcinomas.

BRIEF DESCRIPTION OF THE DRAWINGS

FIGS. 1A-C are analytical HPLC traces of the CH1 inhibitors CH1iA (FIG. 1A), CH1iB (FIG. 1B), and CH1iB-mut (FIG. 1C).

FIGS. 2A-E demonstrate that exogenous CH1 reactivates p53 by blocking the association between HPV16 E6 and p300. Stable polyclonal UMSCC47/empty, UMSCC47/

CH1, SCC90/empty, and SCC90/CH1 cells were generated by transfection and antibiotic selection. FIG. 2A is a pair of western blots showing HPV16 E6-p300 association. Cell lysates were extracted, immunoprecipitated with anti-E6 (left panel) or anti-p300 (right panel) antibody, and immunoblotted with anti-V5, anti-E6, or anti-p300 antibody. Cell lysates were immunoblotted with anti-V5, anti-E6, or anti-p300 antibody for input control. FIG. 2B is a western blot of total and acetylated p53 levels. Cell lysates were immunoblotted with anti-p53 or anti-acetylated[K382]-p53 antibody. FIG. 2C is a graph of p53 transcriptional activity. Cells were co-transfected with a p53 Firefly luciferase reporter plasmid and a control Renilla luciferase plasmid. Firefly luciferase activity was normalized to Renilla luciferase activity to control for transfection efficiency. Data is normalized to empty vector cells and presented as mean±SEM. *$P<0.01$, n=4. FIG. 2D is a pair of graphs of p300 and p53 expression in UMSCC47 (top panel) and SCC90 (bottom panel) cells. FIG. 2E is a pair of graphs of p21, miR-34a, and miR-200c expression in UMSCC47 (top panel) and SCC90 (bottom panel) cells. mRNA expression was determined using qPCR with validated TaqMan assays. Data is normalized to empty vector control cells and presented as mean±SEM. *$P<0.01$, n=3.

FIGS. 3A-H demonstrate that exogenous CH1 has a pleiotropic anti-tumor effect in HPV16-positive HNSCC cells. FIG. 3A is a pair of graphs of cell proliferation. UMSCC47 (left panel) and SCC90 (right panel) cells were treated with control (vehicle) or cis-platinum (10 μM) for 24, 48, and 72 hours. Data is normalized to Day 0 and presented as mean±SEM. *$P<0.01$, control vs. CH1, cis-platinum, or CH1+cis-platinum, **$P<0.01$ CH1 or cis-platinum vs. CH1+cis-platinum, n=6. FIG. 3B is a graph of clonogenic survival. UMSCC47 (left panel) and SCC90 (right panel) were treated with control (vehicle) or cis-platinum (10 μM). Colonies were stained with crystal violet. Data is normalized to empty/control cells and presented as mean±SEM. *$P<0.01$, control vs. CH1, cis-platinum, or CH1+cis-platinum, **$P<0.01$ CH1 or cis-platinum vs. CH1+cis-platinum, n=3. FIG. 3C is a graph of apoptosis. UMSCC47 (left panel) and SCC90 (right panel) were treated with control (vehicle) or cis-platinum (10 μM). FACS was used to quantitate Annexin V-positive apoptotic cells. Data is presented as mean±SEM. *$P<0.01$, control vs. CH1, cis-platinum, or CH1+cis-platinum, **$P<0.01$ CH1 or cis-platinum vs. CH1+cis-platinum, n=3. FIG. 3D is a table of in vivo tumor incidence. Two different dilutions, $3\times10^5$ or $3\times10^4$, of UMSCC47/empty and UMSCC47/CH1 cells were implanted in the flanks of NOD/SCID mice. Tumor incidence was monitored for 49 days following tumor cell implantation. *$P<0.02$, n=8. FIG. 3E is a graph of in vivo tumor growth. Tumors were measured weekly using a digital caliper and tumor volumes were calculated. Data is presented as mean±SEM. *$P<0.01$, n=6. FIG. 3F is a pair of graphs of ALDH (left panel) and CD44 (right panel). ALDH$^{high}$ cells were quantitated using the ALDEFLUOR assay. Data is presented as mean±SEM. *$P<0.01$, n=3. CD44 intensity was determined using FACS with an anti-PE-CD44 antibody and presented as a histogram. FIG. 3G is a pair of graphs of tumorsphere formation efficiency (left panel) and diameter (right panel). Tumorsphere formation efficiency was calculated as the number of tumorspheres (≥50 μm in diameter) formed divided by the original number of cells seeded. Tumorsphere diameter was measured using NIS-Elements software. Data is presented as mean±SEM. *$P<0.01$, n=6. FIG. 3H is a pair of images representative of in vivo tumor incidence of a single tumorsphere. NOD/SCID mice were implanted with a single UMSCC47 tumorsphere (mean diameter of 60-80 μm with ~100 cells) or $1\times10^3$ UMSCC47 cells. A representative UMSCC47 tumorsphere (left image) and the resulting tumor grown in NOD/SCID mice (right image) are shown. Tumor incidence was monitored over a 6 month period. *$P<0.005$, n=1 for single UMSCC47 tumorsphere and n=10 for $1\times10^3$ UMSCC47 cells.

FIGS. 4A-F demonstrate that exogenous CH1 has a pleiotropic anti-tumor effect in HPV-negative HNSCC. Stable polyclonal UMSCC74A/empty and UMSCC74A/CH1 cells were generated by transfection and antibiotic selection. FIG. 4A is a western blot showing total and acetylated p53 levels. Cell lysates were immunoblotted with anti-V5, anti-p53, or anti-acetylated[K382]-p53 antibody. FIG. 4B is a graph of p53 transcriptional activity. Cells were co-transfected with a p53 Firefly luciferase reporter plasmid and a control Renilla luciferase plasmid. Firefly luciferase activity was normalized to Renilla luciferase activity to control for transfection efficiency. Data is normalized to empty vector cells and presented as mean±SEM. *$P<0.01$, n=4. FIG. 4C is a western blot showing MDM2-p300 association. Cell lysates were extracted, immunoprecipitated with anti-p300 antibody, and immunoblotted with anti-MDM2. Cell lysates were immunoblotted with anti-MDM2 or anti-p300 antibody for input control. FIG. 4D is a graph of cell proliferation. Cells were treated with control (vehicle) or cis-platinum (10 μM) for 24 and 48 hours. Data is normalized to Day 0 and presented as mean±SEM. *$P<0.01$, control vs. CH1 or cis-platinum, **$P<0.01$ CH1 or cis-platinum vs. CH1+cis-platinum, n=4. FIG. 4E is a graph of clonogenic survival. Cells were treated with control (vehicle) or cis-platinum (10 μM). Colonies were stained with crystal violet. Data is normalized to empty/control cells and presented as mean±SEM. *$P<0.01$, control vs. CH1, cis-platinum, or CH1+cis-platinum, **$P<0.01$ CH1 or cis-platinum vs. CH1+cis-platinum. FIG. 4F is graph of apoptosis. Cells were treated with control (vehicle) or cis-platinum (10 μM). FACS was used to quantitate Annexin V-positive apoptotic cells. Data is presented as mean±SEM. *$P<0.05$, control vs. CH1, cis-platinum, or CH1+cis-platinum, **$P<0.05$ CH1 or cis-platinum vs. CH1+cis-platinum.

FIGS. 5A-G demonstrate that CH1iB preferentially reactivates p53 in HPV16-positive HNSCC. FIG. 5A is an schematic illustration showing that CH1 has two distinct target sites. HIF1-α/p300 structures were used as guides to design helix mimetics that target site A and site B on the CH1 domain of p300. FIG. 5B shows the structures of the synthetic helices. CH1iA (SEQ ID NO: 7) and CH1iB (SEQ ID NO: 8) were designed to mimic two helices from the C-terminal domain of HIF-1α. The peptides were locked into the helical conformation by the hydrogen bond surrogate method. FIG. 5C is a graph of p53 activity. UMSCC47 (left) and UMSCC74A (right) cells were co-transfected with a p53 Firefly luciferase reporter plasmid and a control Renilla luciferase plasmid. After 24 hours, cells were treated with control (vehicle), CH1iA (10 μM), or CH1iB (10 μM) for 24 hours. Firefly luciferase activity was normalized to Renilla luciferase activity to control for transfection efficiency. Data is normalized to control and presented as mean±SEM. *$P<0.05$, n=3. FIG. 5D is a western blot showing total and acetylated p53 levels. UMSCC47 (left) and UMSCC74A (right) cells were treated with control (vehicle), CH1iA (10 μM), or CH1iB (10 μM) for 24 hours. Cell lysates were immunoblotted with anti-p53 or anti-acetylated[K382]-p53 antibody. FIG. 5E is a pair of graphs of p300, p53, p21, miR-34a, and miR-200c expression.

UMSCC47 (top panel) and UMSCC74A (bottom panel) cells were treated with control (vehicle), CH1iA (10 μM), or CH1iB (10 μM) for 24 hours. mRNA expression was determined using qPCR with validated TaqMan assays. Data is normalized to control cells and presented as mean±SEM. *P<0.01, control vs. CH1iB, n=3. FIG. 5F is a western blot showing HPV16 E6-p300 association. UMSCC47 cells were treated with control (vehicle), CH1iA (10 μM), or CH1iB (10 μM) for 24 hours. Cell lysates were extracted, immunoprecipitated with anti-p300 antibody, and immunoblotted with anti-E6 antibody. Cell lysates were immunoblotted with anti-E6 or anti-p300 antibody for input control. FIG. 5G is a set of graphs of cell proliferation. UMSCC47 (top left panel), UMSCC74A (top right panel), and IMR90 (human normal fibroblasts) (bottom panel) cells were treated with control (vehicle), CH1iA (10 μM), CH1iB (10 μM), cis-platinum (10 μM), CH1iA (10 μM) and cis-platinum (10 μM), or CH1iB (10 μM) and cis-platinum (10 μM) for 24, 48, or 72 hours. Data is normalized to Day 0 and presented as mean±SEM. *P<0.01, control vs. CH1iB or cis-platinum, **P<0.01 CH1iB or cis-platinum vs. CH1iB and cis-platinum, n=6.

FIGS. 6A-F demonstrate that CH1iB potentiates the efficacy of cis-platinum in HPV16-positive HNSCC. FIG. 6A is a western blot showing total and acetylated p53 levels. UMSCC47 cells were treated with control (vehicle), CH1iB (10 μM), cis-platinum (10 μM), or CH1iB (10 μM) and cis-platinum (10 μM) for 24 hours. Cell lysates were immunoblotted with anti-p53 or anti-acetylated[K382]-p53 antibody. FIG. 6B is a graph of p53 transcriptional activity. UMSCC47 cells were co-transfected with a p53 Firefly luciferase reporter plasmid and a control Renilla luciferase plasmid. After 24 hours, cells were treated with control (vehicle), CH1iB (10 μM), cis-platinum (10 μM), or CH1iB (10 μM) and cis-platinum (10 μM) for 24 hours. Firefly luciferase activity was normalized to Renilla luciferase activity to control for transfection efficiency. Data is normalized to control and presented as mean±SEM. *P<0.01, control vs. CH1iB, cis-platinum or CH1iB+cis-platinum, **P<0.01 CH1iB or cis-platinum vs. CH1iB+cis-platinum, n=5. FIG. 6C is a graph of p300, p53, p21, miR-34a, and miR-200c expression. UMSCC47 cells were treated with control (vehicle), CH1iB (10 μM), cis-platinum (10 μM), or CH1iB (10 μM) and cis-platinum (10 μM) for 24 hours. mRNA expression was determined using qPCR with validated TaqMan assays. Data is normalized to control cells and presented as mean±SEM. *P<0.01, control vs. CH1iB, cis-platinum or CH1iB+cis-platinum, **P<0.01 CH1iB or cis-platinum vs. CH1iB+cis-platinum, n=3. FIG. 6D is a pair of graphs of apoptosis. UMSCC47 cells were treated with control (vehicle), CH1iB (10 μM), cis-platinum (10 μM), or CH1iB (10 μM) and cis-platinum (10 μM) for 24 hours. FACS was used to quantitate Annexin V-positive apoptotic cells (left panel). Data is presented as mean±SEM. *P<0.01, control vs. CH1iB, cis-platinum or CH1iB+cis-platinum, **P<0.01 CH1iB or cis-platinum vs. CH1iB+cis-platinum, n=3. FIG. 6E is a series of images and a graph of clonogenic survival. UMSCC47 cells were treated with control (vehicle), CH1iB (10 μM), cis-platinum (10 μM), or CH1iB (10 μM) and cis-platinum (10 μM) at day 0 and colonies were stained with crystal violet at 14 days. Data is normalized to control and presented as mean±SEM. *P<0.01, control vs. CH1iB, cis-platinum or CH1iB+cis-platinum, **P<0.01 CH1iB or cis-platinum vs. CH1iB+cis-platinum, n=3. FIG. 6F is a pair of graphs of tumorsphere formation efficiency (top panel) and diameter (bottom panel). UMSCC47 cells were seeded on low-attachment plates and treated with control (vehicle), CH1iB (10 μM), cis-platinum (3 μM), or CH1iB (10 μM) and cis-platinum (3 μM). Tumorsphere formation efficiency was calculated as the number of tumorspheres (≥50 μm in diameter) formed in 7 days divided by the original number of cells seeded. Tumorsphere diameter was measured using NIS-Elements software. Data is normalized to control and presented as mean±SEM. *P<0.01, control vs. CH1iB, cis-platinum or CH1iB+cis-platinum, **P<0.01 CH1iB or cis-platinum vs. CH1iB+cis-platinum, n=8.

FIGS. 7A-B relate to the effect of CH1iB-mut, an inactive analog of CH1iB, on p53 transcriptional activity and cell proliferation. FIG. 7A is a graph of p53 transcriptional activity. UMSCC47 cells were co-transfected with a p53 Firefly luciferase reporter plasmid and a control Renilla luciferase plasmid. After 24 hours, cells were treated with control (vehicle) or CH1iB-mut (10 μM) for 24 hours. Firefly luciferase activity was normalized to Renilla luciferase activity to control for transfection efficiency. Data is presented as mean±SEM. *P<0.05, n=5. FIG. 7B is a graph of cell proliferation. UMSCC47 cells were treated with control (vehicle), CH1iB-mut (10 μM), cis-platinum (10 μM), or CH1iB-mut (10 μM) and cis-platinum (10 μM) for 24 or 48 hours. Data is normalized to Day 0 and presented as mean±SEM. *P<0.01, control or CH1iB-mut vs. cis-platinum or cis-platinum+CH1iB-mut, n=6.

DETAILED DESCRIPTION OF THE INVENTION

The incidence of human papillomavirus (HPV)-positive head and neck squamous cell carcinoma (HNSCC) has rapidly increased over the past 30 years prompting the suggestion that an epidemic may be on the horizon. Therefore, there is a clinical need to develop alternate therapeutic strategies to manage the growing number of HPV-positive HNSCC patients, as well as other HPV-associated cancers. E6, the oncogenic protein of high-risk HPV serotypes, inactivates p53 through two distinct mechanisms: association with E6AP to degrade p53 and association with p300 to block p300-mediated p53 acetylation and activation. As described herein targeting the E6-p300 interaction is an effective approach to reactivate p53 in HPV-positive cancers. Ectopic expression of the CH1 domain of p300 in HPV-positive HNSCC blocks the association between E6 and p300, increases total and acetylated p53 levels, and enhances p53 transcriptional activity. Moreover, expression of p21, miR-34a, and miR-200c are increased, demonstrating functional p53 reactivation. CH1 overexpression in HPV-positive HNSCC has a global anti-cancer effect resulting in a decrease in cell proliferation and clonogenic survival and an increase in apoptosis. The in vivo tumor initiating ability of HPV-positive HNSCC is severely compromised with CH1 overexpression, in part through a reduction in the cancer initiating cell population. Peptidomimetics that target the CH1 domain of p300 disrupt the E6-p300 interaction, reactivating p53, and potentiate the anti-cancer activity of cis-platinum in HPV-positive cancer cells. The peptidomimetics described herein represent a class of p53 reactivation therapeutics for managing HPV-positive cancer patients.

The present invention relates to a peptidomimetic, wherein the peptidomimetic:
(i) mimics a helix having the formula $X_1$-$X_2$-$X_2$-$X_3$-$X_2$-$X_2$-$X_1$-$X_4$, wherein each $X_1$ is any negatively charged residue, each $X_2$ is any hydrophobic residue, $X_3$ is any positively-charged residue, and $X_4$ is any polar residue; and (ii) is selected from the group consisting of:
 (a) a compound of Formula I:

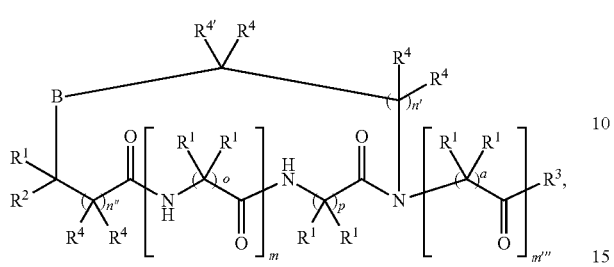

I wherein:
B is $C(R^1)_2$, O, S, or $NR^1$;
each $R^1$ is independently hydrogen, an amino acid side chain, an alkyl, an alkenyl, an alkynyl, a cycloalkyl, a heterocyclyl, an aryl, a heteroaryl, or an arylalkyl;
$R^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; $-OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; $-(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

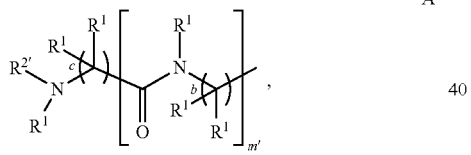

A wherein:
$R^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; $-OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or $-(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
m' is zero or any number;
each b is independently one or two; and
c is one or two;
$R^3$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; $-OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; $-N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

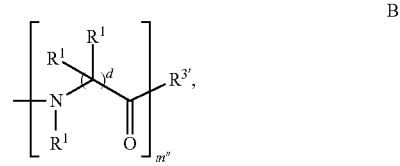

B wherein:
$R^{3'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; $-OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or $-N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
m" is zero or any number; and
each d is independently one or two;
each $R^4$ is independently hydrogen, an alkyl, an alkenyl, an alkynyl, a cycloalkyl, a heterocyclyl, an aryl, a heteroaryl, or an arylalkyl;
$R^{4'}$ is hydrogen, an alkyl, an alkenyl, an alkynyl, a cycloalkyl, a heterocyclyl, an aryl, a heteroaryl, an arylalkyl, or a double bond between $C(R^{4'},R^4)$ and B;
a is one or two;
m, n', and n" are each independently zero, one, two, three, or four;
m'" is zero or one;
each o is independently one or two; and
p is one or two;
(b) a compound of Formula II:

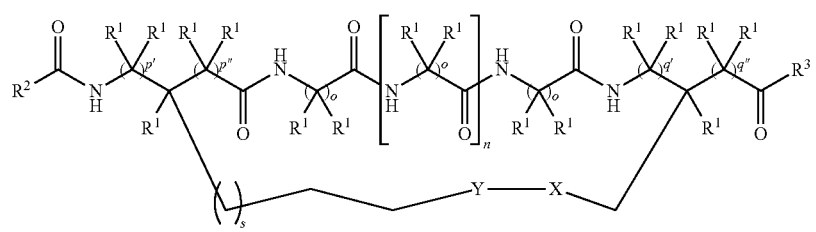

II wherein:

each $R^1$ is independently hydrogen, an amino acid side chain, an alkyl, an alkenyl, an alkynyl, a cycloalkyl, a heterocyclyl, an aryl, a heteroaryl, or an arylalkyl;

$R^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

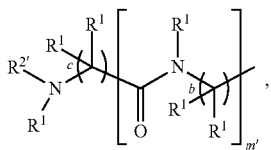

A wherein:

$R^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

m' is zero or any number;

each b is independently one or two; and c is one or two;

$R^3$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

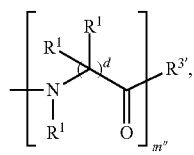

B wherein:

$R^{3'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —$N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

m" is zero or any number; and each d is independently one or two;

n is one or four;

each o is independently one or two;

one of p' and p" is zero and the other is zero or one;

one of q' and q" is zero and the other is zero or one;

s is one, two, three, four, or five; and

Y—X is a hydrocarbon, an amide bond, an alkane, an alkene, an alkyne, a triazole, or a disulfide bond; and (c) a compound of Formula III:

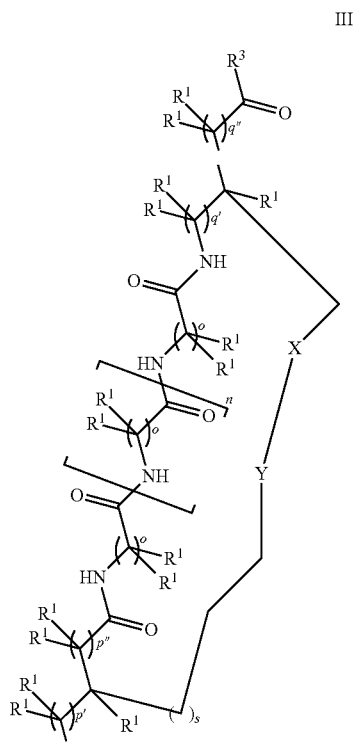

III

-continued

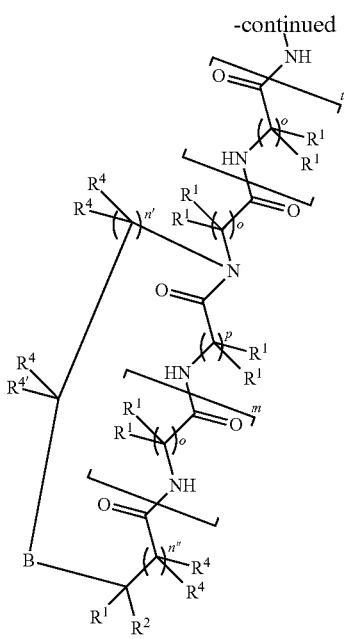

wherein:

B is C(R$^1$)$_2$, O, S, or NR$^1$;

each R$^1$ is independently hydrogen, an amino acid side chain, an alkyl, an alkenyl, an alkynyl, a cycloalkyl, a heterocyclyl, an aryl, a heteroaryl, or an arylalkyl;

R$^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR$^5$ wherein R$^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —(CH$_2$)$_{0-1}$N(R$^5$)$_2$ wherein each R$^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

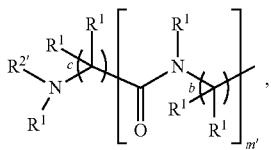

wherein:

R$^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR$^5$ wherein R$^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —(CH$_2$)$_{0-1}$N(R$^5$)$_2$ wherein each R$^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

m' is zero or any number;
each b is independently one or two; and
c is one or two;

R$^3$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR$^5$ wherein R$^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —N(R$^5$)$_2$ wherein each R$^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

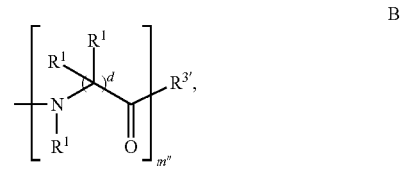

wherein:

R$^{3'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR$^5$ wherein R$^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —N(R$^5$)$_2$ wherein each R$^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

m" is zero or any number; and
each d is independently one or two;

each R$^4$ is independently hydrogen, an alkyl, an alkenyl, an alkynyl, a cycloalkyl, a heterocyclyl, an aryl, a heteroaryl, or an arylalkyl;

R$^{4'}$ is hydrogen, an alkyl, an alkenyl, an alkynyl, a cycloalkyl, a heterocyclyl, an aryl, a heteroaryl, an arylalkyl, or a double bond between C(R$^{4'}$,R$^4$) and B;

m, n', and n" are each independently zero, one, two, three, or four;

n is one or four;

each o is independently one or two;

p is one or two;

one of p' and p" is zero and the other is zero or one;

one of q' and q" is zero and the other is zero or one;

s is one, two, three, four, or five; and

Y—X is a hydrocarbon, an amide bond, an alkane, an alkene, an alkyne, a triazole, or a disulfide bond.

Amino acid side chains according to this and all aspects of the present invention can be any amino acid side chain from natural or nonnatural amino acids, including from alpha amino acids, beta amino acids, gamma amino acids, L-amino acids, and D-amino acids.

As used herein, the term "alkyl" means an aliphatic hydrocarbon group which may be straight or branched having about 1 to about 6 carbon atoms in the chain. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Exemplary alkynyl groups include ethynyl, propynyl, n-butynyl, 2-butynyl, 3-methyl-butynyl, and n-pentynyl.

As used herein, the term "cycloalkyl" refers to a non-aromatic saturated or unsaturated mono- or polycyclic ring system which may contain 3 to 6 carbon atoms, and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

As used herein, the term "heterocyclyl" refers to a stable 3- to 18-membered ring system that consists of carbon atoms and from one to five heteroatoms selected from the group consisting of nitrogen, oxygen, and sulfur. The heterocyclyl may be a monocyclic or a polycyclic ring system, which may include fused, bridged, or spiro ring systems; and the nitrogen, carbon, or sulfur atoms in the heterocyclyl may be optionally oxidized; the nitrogen atom may be optionally quaternized; and the ring may be partially or fully saturated. Representative monocyclic heterocyclyls include piperidine, piperazine, pyrimidine, morpholine, thiomorpholine, pyrrolidine, tetrahydrofuran, pyran, tetrahydropyran, oxetane, and the like. Representative polycyclic heterocyclyls include indole, isoindole, indolizine, quinoline, isoquinoline, purine, carbazole, dibenzofuran, chromene, xanthene, and the like.

As used herein, the term "aryl" refers to an aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

As used herein, "heteroaryl" refers to an aromatic ring radical which consists of carbon atoms and from one to five heteroatoms selected from the group consisting of nitrogen, oxygen, and sulfur. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl. Additional heteroaryls are described in COMPREHENSIVE HETEROCYCLIC CHEMISTRY: THE STRUCTURE, REACTIONS, SYNTHESIS AND USE OF HETEROCYCLIC COMPOUNDS (Katritzky et al. eds., 1984), which is hereby incorporated by reference in its entirety.

The term "arylalkyl" refers to a moiety of the formula —$R^a R^b$ where $R^a$ is an alkyl or cycloalkyl as defined above and $R^b$ is an aryl or heteroaryl as defined above.

As used herein, the term "acyl" means a moiety of formula R-carbonyl, where R is an alkyl, cycloalkyl, aryl, or heteroaryl as defined above. Exemplary acyl groups include formyl, acetyl, propanoyl, benzoyl, and propenoyl.

An amino acid according to this and all aspects of the present invention can be any natural or non-natural amino acid.

A "peptide" as used herein is any oligomer of two or more natural or non-natural amino acids, including alpha amino acids, beta amino acids, gamma amino acids, L-amino acids, D-amino acids, and combinations thereof. In preferred embodiments, the peptide is ~5 to ~30 (e.g., ~5 to ~10, ~5 to ~17, ~10 to ~17, ~10 to ~30, or ~18 to ~30) amino acids in length. Typically, the peptide is 10-17 amino acids in length. In a preferred embodiment, the peptide contains a mixture of alpha and beta amino acids in the pattern α3/β1 (this is particularly preferred for α-helix mimetics).

A "tag" as used herein includes any labeling moiety that facilitates the detection, quantitation, separation, and/or purification of the compounds of the present invention. Suitable tags include purification tags, radioactive or fluorescent labels, and enzymatic tags.

Purification tags, such as poly-histidine ($His_{6-}$), a glutathione-S-transferase (GST–), or maltose-binding protein (MBP–), can assist in compound purification or separation but can later be removed, i.e., cleaved from the compound following recovery. Protease-specific cleavage sites can be used to facilitate the removal of the purification tag. The desired product can be purified further to remove the cleaved purification tags.

Other suitable tags include radioactive labels, such as, $^{125}I$, $^{131}I$, $^{111}In$, or $^{99}TC$. Methods of radiolabeling compounds are known in the art and described in U.S. Pat. No. 5,830,431 to Srinivasan et al., which is hereby incorporated by reference in its entirety. Radioactivity is detected and quantified using a scintillation counter or autoradiography. Alternatively, the compound can be conjugated to a fluorescent tag. Suitable fluorescent tags include, without limitation, chelates (europium chelates), fluorescein and its derivatives, rhodamine and its derivatives, dansyl, Lissamine, phycoerythrin, and Texas Red. The fluorescent labels can be conjugated to the compounds using techniques disclosed in CURRENT PROTOCOLS IN IMMUNOLOGY (Coligen et al. eds., 1991), which is hereby incorporated by reference in its entirety. Fluorescence can be detected and quantified using a fluorometer.

Enzymatic tags generally catalyze a chemical alteration of a chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Examples of suitable enzymatic tags include luciferases (e.g., firefly luciferase and bacterial luciferase; see e.g., U.S. Pat. No. 4,737,456 to Weng et al., which is hereby incorporated by reference in its entirety), luciferin, 2,3-dihydrophthalazinediones, malate dehydrogenase, urease, peroxidases (e.g., horseradish peroxidase), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase, microperoxidase, and the like. Techniques for conjugating enzymes to proteins and peptides are described in O'Sullivan et al., *Methods for the Preparation of Enzyme—Antibody Conjugates for Use in Enzyme Immunoassay*, in METHODS IN ENZYMOLOGY 147-66 (Langone et al. eds., 1981), which is hereby incorporated by reference in its entirety.

A targeting moiety according to the present invention functions to (i) promote the cellular uptake of the compound, (ii) target the compound to a particular cell or tissue type (e.g., signaling peptide sequence), or (iii) target the compound to a specific sub-cellular localization after cellular uptake (e.g., transport peptide sequence).

To promote the cellular uptake of a compound of the present invention, the targeting moiety may be a cell penetrating peptide (CPP). CPPs translocate across the plasma membrane of eukaryotic cells by a seemingly energy-independent pathway and have been used successfully for intracellular delivery of macromolecules, including antibodies, peptides, proteins, and nucleic acids, with molecular weights several times greater than their own. Several commonly used CPPs, including polyarginines, transportant, protamine, maurocalcine, and M918, are suitable targeting moieties for use in the present invention and are well known in the art (see Stewart et al., "Cell-Penetrating Peptides as Delivery Vehicles for Biology and Medicine," *Organic Biomolecular Chem.* 6:2242-2255 (2008), which is hereby incorporated by reference in its entirety). Additionally, methods of making CPP are described in U.S. Patent Application Publication No. 20080234183 to Hallbrink et al., which is hereby incorporated by reference in its entirety.

Another suitable targeting moiety useful for enhancing the cellular uptake of a compound is an "importation competent" signal peptide as disclosed by U.S. Pat. No. 6,043,339 to Lin et al., which is hereby incorporated by reference in its entirety. An importation competent signal peptide is generally about 10 to about 50 amino acid residues in length—typically hydrophobic residues—that render the compound capable of penetrating through the cell membrane from outside the cell to the interior of the cell. An exemplary importation competent signal peptide includes the signal peptide from Kaposi fibroblast growth factor (see U.S. Pat. No. 6,043,339 to Lin et al., which is hereby incorporated by reference in its entirety). Other suitable peptide sequences can be selected from the SIGPEP database (see von Heijne G., "SIGPEP: A Sequence Database for Secretory Signal Peptides," *Protein Seq. Data Anal.* 1(1):41-42 (1987), which is hereby incorporated by reference in its entirety).

Another suitable targeting moiety is a signal peptide sequence capable of targeting the compounds of the present invention to a particular tissue or cell type. The signaling peptide can include at least a portion of a ligand binding protein. Suitable ligand binding proteins include high-affinity antibody fragments (e.g., Fab, Fab' and F(ab')$_2$, single-chain Fv antibody fragments), nanobodies or nanobody fragments, fluorobodies, or aptamers. Other ligand binding proteins include biotin-binding proteins, lipid-binding proteins, periplasmic binding proteins, lectins, serum albumins, enzymes, phosphate and sulfate binding proteins, immunophilins, metallothionein, or various other receptor proteins. For cell specific targeting, the signaling peptide is preferably a ligand binding domain of a cell specific membrane receptor. Thus, when the modified compound is delivered intravenously or otherwise introduced into blood or lymph, the compound will adsorb to the targeted cell, and the targeted cell will internalize the compound. For example, if the target cell is a cancer cell, the compound may be conjugated to an anti-C3B(I) antibody as disclosed by U.S. Pat. No. 6,572,856 to Taylor et al., which is hereby incorporated by reference in its entirety. Alternatively, the compound may be conjugated to an alphafeto protein receptor as disclosed by U.S. Pat. No. 6,514,685 to Moro, which is hereby incorporated by reference in its entirety, or to a monoclonal GAH antibody as disclosed by U.S. Pat. No. 5,837,845 to Hosokawa, which is hereby incorporated by reference in its entirety. For targeting a compound to a cardiac cell, the compound may be conjugated to an antibody recognizing elastin microfibril interfacer (EMILIN2) (Van Hoof et al., "Identification of Cell Surface for Antibody-Based Selection of Human Embryonic Stem Cell-Derived Cardiomyocytes," *J Proteom Res* 9:1610-18 (2010), which is hereby incorporated by reference in its entirety), cardiac troponin I, connexin-43, or any cardiac cell-surface membrane receptor that is known in the art. For targeting a compound to a hepatic cell, the signaling peptide may include a ligand domain specific to the hepatocyte-specific asialoglycoprotein receptor. Methods of preparing such chimeric proteins and peptides are described in U.S. Pat. No. 5,817,789 to Heartlein et al., which is hereby incorporated by reference in its entirety.

Another suitable targeting moiety is a transport peptide that directs intracellular compartmentalization of the compound once it is internalized by a target cell or tissue. For transport to the endoplasmic reticulum (ER), for example, the compound can be conjugated to an ER transport peptide sequence. A number of such signal peptides are known in the art, including the signal peptide MMSFVSLLLVGIL-FYATEAEQLTKCEVFQ (SEQ ID NO: 1). Other suitable ER signal peptides include the N-terminus endoplasmic reticulum targeting sequence of the enzyme 17β-hydroxysteroid dehydrogenase type 11 (Horiguchi et al., "Identification and Characterization of the ER/Lipid Droplet-Targeting Sequence in 17β-hydroxysteroid Dehydrogenase Type 11," *Arch. Biochem. Biophys.* 479(2):121-30 (2008), which is hereby incorporated by reference in its entirety), or any of the ER signaling peptides (including the nucleic acid sequences encoding the ER signal peptides) disclosed in U.S. Patent Application Publication No. 20080250515 to Reed et al., which is hereby incorporated by reference in its entirety. Additionally, the compound of the present invention can contain an ER retention signal, such as the retention signal KEDL (SEQ ID NO: 2). Methods of modifying the compounds of the present invention to incorporate transport peptides for localization of the compounds to the ER can be carried out as described in U.S. Patent Application Publication No. 20080250515 to Reed et al., which is hereby incorporated by reference in its entirety.

For transport to the nucleus, the compounds of the present invention can include a nuclear localization transport signal. Suitable nuclear transport peptide sequences are known in the art, including the nuclear transport peptide PPKKKRKV (SEQ ID NO:3). Other nuclear localization transport signals include, for example, the nuclear localization sequence of acidic fibroblast growth factor and the nuclear localization sequence of the transcription factor NF-KB p50 as disclosed by U.S. Pat. No. 6,043,339 to Lin et al., which is hereby incorporated by reference in its entirety. Other nuclear localization peptide sequences known in the art are also suitable for use in the compounds of the present invention.

Suitable transport peptide sequences for targeting to the mitochondria include MLSLRQSIRFFKPATRTLCSSRYLL (SEQ ID NO: 4). Other suitable transport peptide sequences suitable for selectively targeting the compounds of the present invention to the mitochondria are disclosed in U.S. Patent Application Publication No. 20070161544 to Wipf, which is hereby incorporated by reference in its entirety.

The peptidomimetics of the present invention are designed to mimic a helix having the formula $X_1$-$X_2$-$X_2$-$X_3$-$X_2$-$X_2$-$X_1$-$X_4$, where each $X_1$ is any negatively charged residue, each $X_2$ is any hydrophobic residue, $X_3$ is any positively-charged residue, and $X_4$ is any polar residue. In a preferred embodiment, the peptidomimetic mimics a helix having the formula $X_1$-$X_2$-L-$X_3$-$X_2$-L-$X_1$-$X_4$. In a preferred embodiment, the peptidomimetic mimics a helix having the formula $X_1$-$X_2$-L-$X_3$-$X_2$-L-$X_1$-Q. In a preferred embodiment, the peptidomimetic mimics a helix having the formula XELA*RALDQ (SEQ ID NO: 8), where X is 4-pentenoic acid and A* is N-allylalanine.

As will be apparent to those of ordinary skill in the art, when $R^2$ and/or $R^3$ are a moiety of the recited formulae, the overall size of the compounds of Formula I, Formula II, and Formula III can be adjusted by varying the values of m' and/or m", which are independently zero or any number. Typically, m' and m" are independently from zero to about thirty (e.g., 0 to ~18, 0 to ~10, 0 to ~5, ~5 to ~30, ~5 to ~18, ~5 to ~10, ~8 to ~30, ~8 to ~18, ~8 to ~10, ~10 to ~18, or ~10 to ~30). In one embodiment of compounds of Formula I, m' and m" are independently 4-10. In another embodiment of compounds of Formula I, m' and m" are independently 5-6.

As will be apparent to the skilled artisan, compounds of Formula I and Formula III include a diverse range of helical conformation, which depends on the values of m, n', and n".

These helical conformations include $3_{10}$-helices (e.g., m=0 and n'+n"=2), α-helices (e.g., m=1 and n'+n"=2), n-helices (e.g., m=2 and n'+n"=2), and gramicidin helices (e.g., m=4 and n'+n"=2). In a preferred embodiment, the number of atoms in the backbone of the helical macrocycle is 12-15, more preferably 13 or 14.

In at least one embodiment of compounds of Formula I, m'" is one and a is two.

In at least one embodiment, $R^2$ is: a beta amino acid, a moiety of Formula A where m' is at least one and at least one b is two, a moiety of Formula A where c is two, or a moiety of Formula A where $R^{2'}$ is a beta amino acid. In at least one embodiment, $R^3$ is: a beta amino acid, a moiety of Formula B where m" is at least one and at least one d is two, or a moiety of Formula B where $R^{3'}$ is a beta amino acid. Combinations of these embodiments are also contemplated.

When $R^2$ is a moiety of Formula A, m' is preferably any number from one to 19. When $R^3$ is a moiety of Formula B, m" is preferably any number from one to nine.

In preferred embodiments, the compound is a compound of Formula IA, Formula IIA, or Formula IIIA (i.e., a helix cyclized at the N-terminal); Formula IB, Formula IIB, or Formula IIIB (i.e., a helix cyclized mid-peptide); or Formula IC, Formula IIC, or Formula IIIC (i.e., a helix cyclized at the C-terminal):

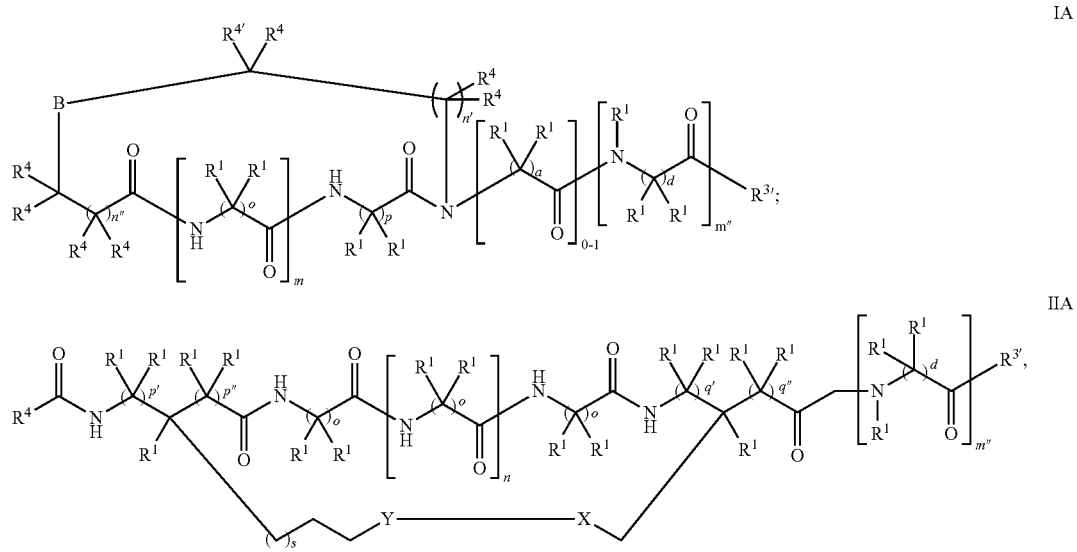

where $R^4$ is independently hydrogen, an alkyl, an alkenyl, an alkynyl, a cycloalkyl, a heterocyclyl, an aryl, a heteroaryl, or an arylalkyl;

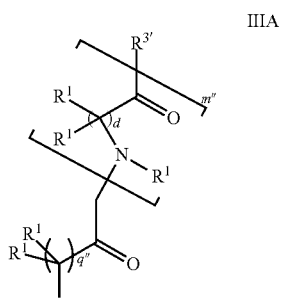

-continued
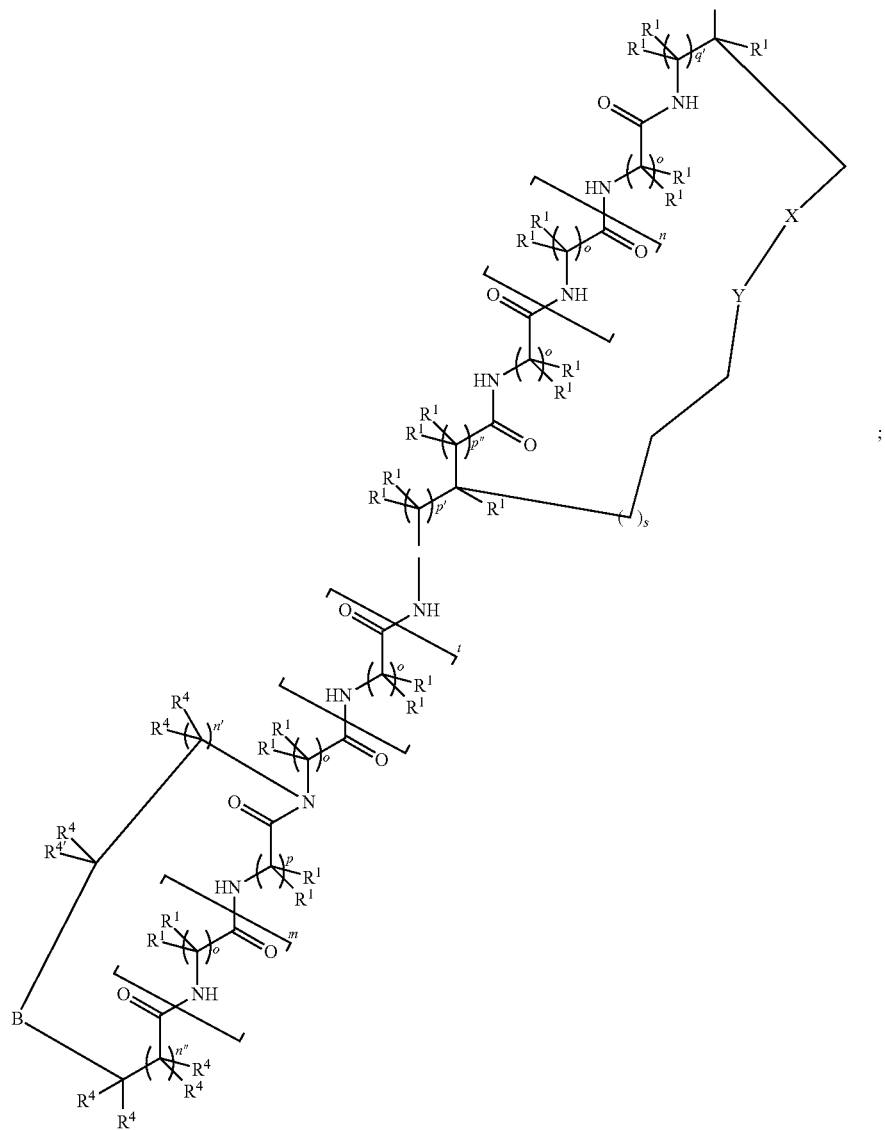
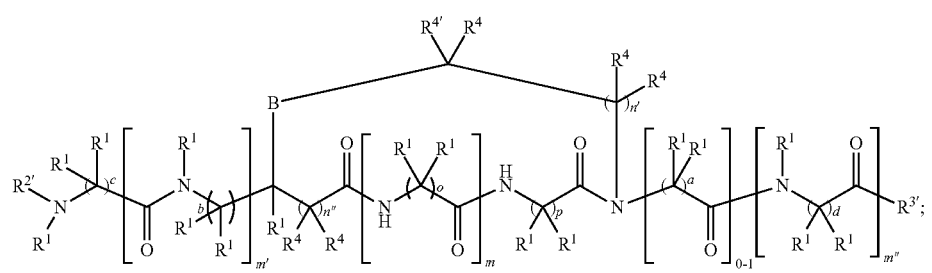
IB
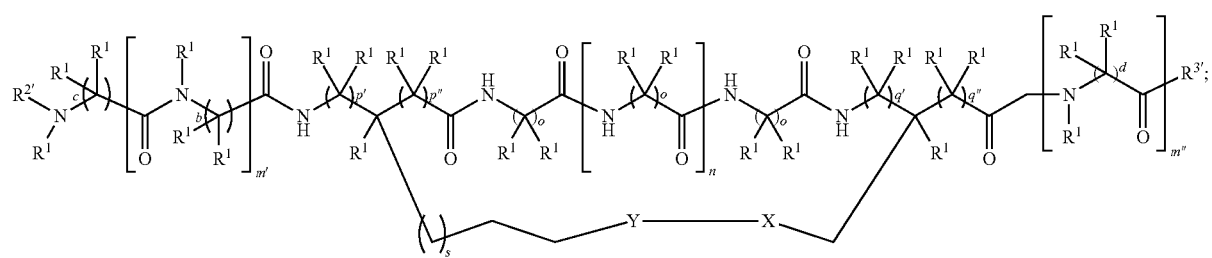
IIB

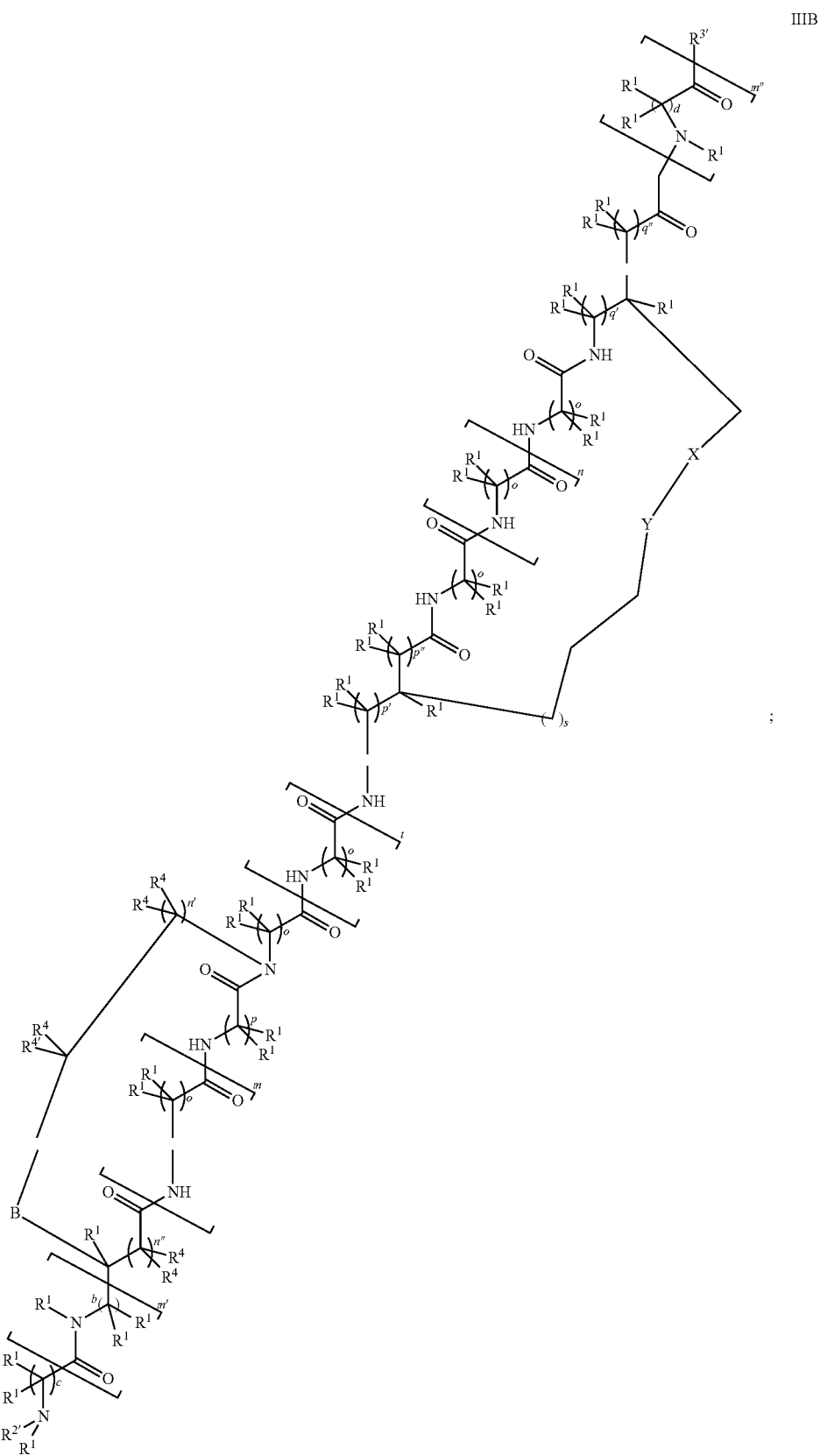

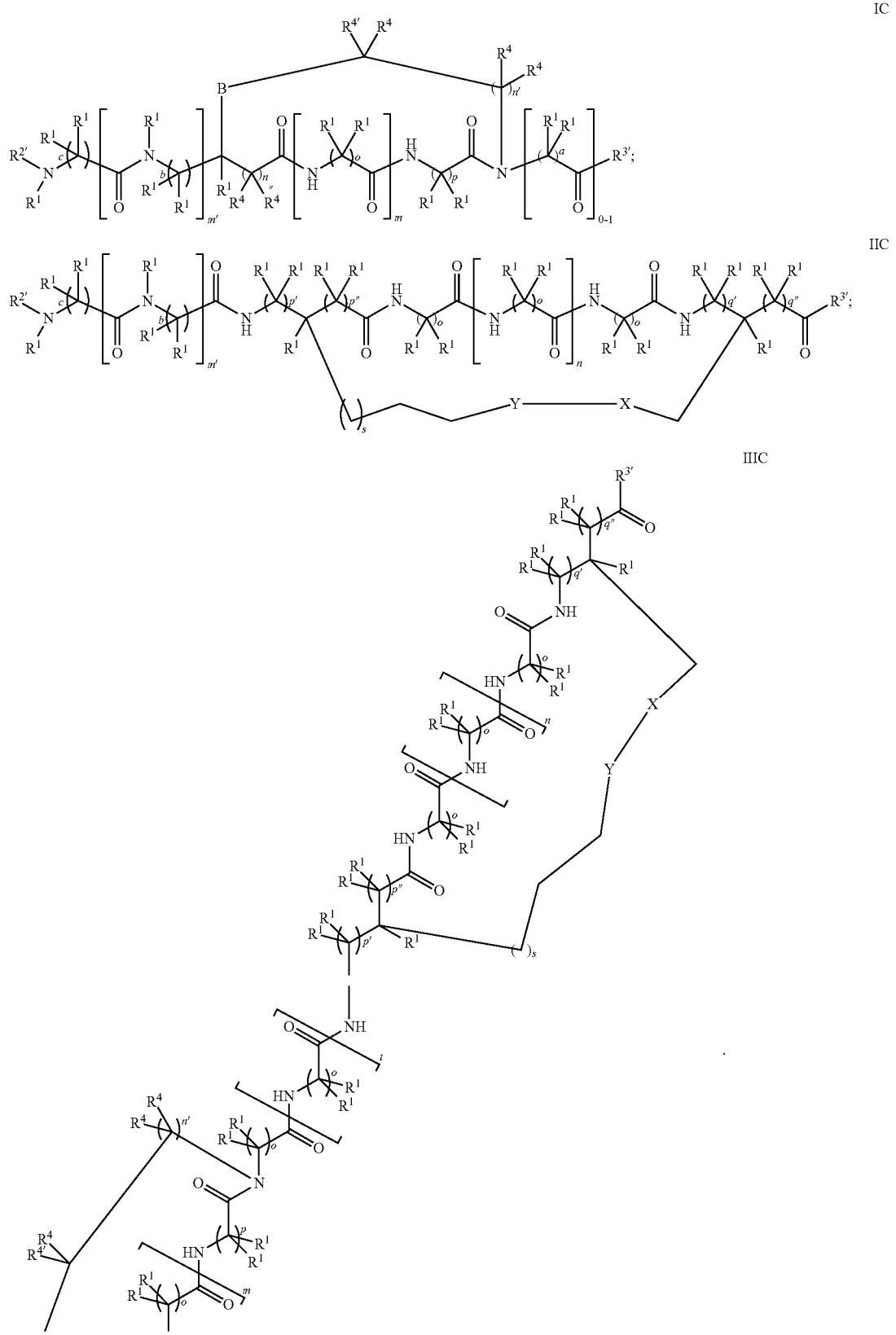

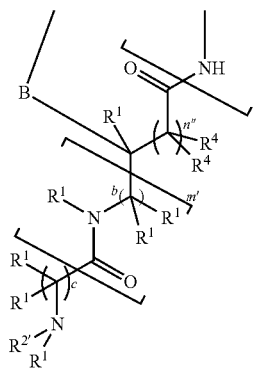

As will be apparent to the skilled artisan, the pattern of β substitution in the attached peptides of the peptidomimetics of Formulae I, II, and III can be controlled by adjusting the values for m''' and a (when the peptidomimetic is a compound of Formula I), as well as m', b, and c (when $R^2$ is a moiety of Formula A), and m'' and d (when $R^3$ is a moiety of Formula B). Substitution in peptidomimetics of Formulae IA, IIA, IIIA, IB, IIB, IIIB, IC, IIC, and IIIC can further be controlled as will be apparent to the skilled artisan. In a preferred embodiment, the attached peptide has the formula α3/β1.

The peptidomimetics of the present invention may be prepared using methods that are known in the art. By way of example, peptidomimetics of Formula I, which contain a hydrogen bond surrogate, may be prepared using the methods disclosed in, e.g., U.S. patent application Ser. No. 11/128,722, U.S. patent application Ser. No. 13/724,887, and Mahon & Arora, "Design, Synthesis, and Protein-Targeting Properties of Thioether-Linked Hydrogen Bond Surrogate Helices," *Chem. Commun.* 48:1416-18 (2012), each of which is hereby incorporated by reference in its entirety. Peptidomimetics of Formula II, which contain a side-chain constraint, may be prepared using the methods disclosed in, e.g., Schafineister et al., *J. Am. Chem. Soc.* 122:5891 (2000); Sawada & Gellman, *J. Am. Chem. Soc.* 133:7336 (2011); Patgiri et al., *J. Am. Chem. Soc.* 134:11495 (2012); Henchey et al., *Curr. Opin. Chem. Biol.* 12:692 (2008); Harrison et al., *Proc. Nat'l Acad. Sci. U.S.A.* 107: 11686 (2010); Shepherd et al., *J. Am. Chem. Soc.* 127:2974 (2005); Phelan et al., *J. Am. Chem. Soc.* 119:455 (1997); Jackson et al., *J. Am. Chem. Soc.* 113:9391 (1991); Blackwell & Grubbs, *Angew. Chem. Int'l. Ed. Engl.* 37:3281 (1998), each of which is hereby incorporated by reference in its entirety. Peptidomimetics of Formula III, which contain both a hydrogen bond surrogate and a side-chain constraint, may be prepared using a combination of the above methods.

Another aspect of the present invention relates to pharmaceutical formulations comprising any of the above described peptidomimetics of Formula I, Formula II, or Formula III of the present invention (including the peptidomimetics of Formulae IA, IIA, IIIA, IB, IIB, IIIB, IC, IIC, and IIIC) and a pharmaceutically acceptable carrier. Acceptable pharmaceutical carriers include solutions, suspensions, emulsions, excipients, powders, or stabilizers. The carrier should be suitable for the desired mode of delivery.

In addition, the pharmaceutical formulations of the present invention may further comprise one or more pharmaceutically acceptable diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

Another aspect of the present invention relates to a method of treating or preventing in a subject a disorder mediated by interaction of E6 with CREB-binding protein and/or p300, the method comprising administering to the subject a peptidomimetic of the present invention under conditions effective to treat or prevent the disorder.

Disorders mediated by the interaction of E6 with CREB-binding protein and/or p300 include, for example, HPV-associated cancers. HPV-associated cancers are those that are caused (at least in part) by high-risk, or oncogenic, HPV types, e.g., HPV-16, HPV-18, HPV-31, HPV-33, HPV-35, HPV-39, HPV-45, HPV-51, HPV-52, HPV-56, HPV-58, HPV-59, HPV-68, HPV-69, HPV-73, and HPV-82. These cancers include anogenital cancers, including cervical cancer, vulvar cancer, vaginal cancer, penile cancer, anal cancer, as well as cancers of the head and neck, including HNSCC and oropharyngeal cancer.

The subject according to this aspect of the present invention is preferably a human subject.

The compounds of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

As indicated by Example 18 below, the peptidomimetics of the present invention can potentiate the anti-cancer effect of other anti-cancer agents. Thus, in some embodiments, the peptidomimetics are used together with one or more other anti-cancer agents. Suitable agents include, without limitation, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane, Actinomycin-D, Adcetris, Adriamycin, Adrucil, Afinitor, Agrylin, Ala-Cort, Aldesleukin, Alemtuzumab, ALIMTA, Alitretinoin, Alkaban-AQ, Alkeran, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Axitinib, Azacitidine, BCG, Bendamustine, Bevacizumab, Bexarotene, BEXXAR®, Bicalutamide, BiCNU, Blenoxane®, Bleomycin, Bortezomib, Bosulif, Bosutinib, Brentuximab Vedotin, Busulfan, Busulfex®, C225, Cabazitaxel, Cabozantinib, Calcium Leucovorin, Campath®, Camptosar®, Camptothecin-11, Capecitabine, Caprelsa, Carac™, Carboplatin, Carfilzomib, Carmustine, Carmustine Wafer, Casodex®, CC-5013, CCI-779, CCNU, CDDP, CeeNU, Cerubidine®, Cetuximab, Chlorambucil, Cisplatin, Cisplatinum, Citrovorum Factor, Cladribine, Cometriq, Cortisone, Cosmegen®, CPT-11, Crizotinib, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, daunorubicin-hydrochloride, Daunorubicin Liposomal, DaunoXome®, Decadron, Decitabine, Delta-Cortef®, Deltasone®, Denileukin Diftitox, Denosumab, DepoCyt™, Dexamethasone, Dexamethasone Acetate, Dexamethasone Sodium Phosphate, Dexasone, Dexrazoxane, DHAD, DIC, Diodex, Docetaxel, Doxorubicin, Doxorubicin Liposomal, Droxia™, DTIC, DTIC-Dome®, Duralone®, Eculizumab, Efudex®, Ellence™, Eloxatin™, Elspar®, Emcyt®, Epirubicin, Epoetin Alfa, Erbitux, Eribulin, Erivedge, Erlotinib, Erwinia L-asparaginase, Estramustine, Ethyol, Etopophos, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, Folotyn, FUDR®, Fulvestrant, G-CSF, Gefitinib, Gemcitabine, Gemtuzumab ozogamicin, Gemzar, Gleevec™, Gliadel Wafer®, GM-CSF, Goserelin, Granulocyte—Colony Stimulating Factor, Granulocyte Macrophage Colony Stimulating Factor, Halaven®, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin, ICLUSIG®, Ifex®, IFN-alpha, Ifosfamide, IL-11, IL-2, Imatinib Mesylate, Imidazole Carboxamide, Inlyta®, Interferon-Alfa, Interferon Alfa-2b (PEG Conjugate), Interleukin-2, Interleukin-11, Intron A® (interferon alfa-2b), Ipilimumab, Irinotecan, Isotretinoin, Istodax, Ixabepilone, Jevtana, Kidrolase, Kyprolis, Lanacort, Lapatinib, L-asparaginase, LCR, Lenalidomide, Letrozole, Leucovorin, Leukeran, Leukine, Leuprolide, Leucrocristine, Leustatin, Liposomal Ara-C, Liquid Pred, Lomustine, L-PAM, L-Sarcolysin, Lupron, Lupron Depot, Marqibo, Matulane, Maxidex, Mechlorethamine, Mechlorethamine Hydrochloride, Medralone, Medrol, Megace, Megestrol, Megestrol Acetate, Melphalan, Mercaptopurine, Mesna, Mesnex, Methotrexate, Methotrexate Sodium, Methylprednisolone, Meticorten, Mitomycin, Mitomycin-C, Mitoxantrone, M-Prednisol, MTC, MTX, Mustargen, Mustine, Mutamycin, Myleran, Mylocel, Mylotarg, Navelbine, Nelarabine, Neosar, Neulasta, Neumega, Neupogen, Nexavar, Nilandron, Nilotinib, Nilutamide, Nipent, Nitrogen Mustard, Novaldex, Novantrone, Nplate, Octreotide, Octreotide Acetate, Ofatumumab, Oncospar, Oncovin, Ontak, Onxal, Oprelvekin, Oraprel, Orasone, Oxaliplatin, Paclitaxel, Paclitaxel Protein-bound, Pamidronate, Panitumumab, Panretin, Paraplatin, Pazopanib, Pediapred, PEG Interferon, Pegaspargase, Pegfilgrastim, PEG-INTRON, PEG-L-asparaginase, PEMETREXED, Pentostatin, Perjeta, Pertuzumab, Phenylalanine Mustard, Platinol, Platinol-AQ, Ponatinib, Pralatrexate, Prednisolone, Prednisone, Prelone, Procarbazine, PROCRIT, Proleukin, Prolia, Prolifeprospan 20 with Carmustine Implant, Provenge, Purinethol, Raloxifene, Regorafenib, Revlimid, Rheumatrex, Rituxan, Rituximab, Roferon-A (Interferon Alfa-2a), Romidepsin, Romiplostim, Rubex, Rubidomycin Hydrochloride, Sandostatin, Sandostatin LAR, Sargramostim, Sipuleucel-T, Soliris, Solu-Cortef, Solu-Medrol, Sorafenib, SPRYCEL, STI-571, Stivarga, Streptozocin, SU11248, Sunitinib, Sutent, Tamoxifen, Tarceva, Targretin, Tasigna, Taxol, Taxotere, Temodar, Temozolomide, Temsirolimus, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Torisel, Tositumomab, Trastuzumab, Treanda, Tretinoin, Trexall, Trisenox, TSPA, TYKERB, Valrubicin, Valstar, Vandetanib, VCR, Vectibix, Velban, Velcade, VePesid, Vesanoid, Viadur, Vidaza, Vinblastine, Vinblastine Sulfate, Vincasar Pfs, Vincristine, Vincristine Liposomal, Vinorelbine, Vinorelbine Tartrate, Vismodegib, VLB, VM-26, Vorinostat, Votrient, VP-16, Vumon, Xalkori Capsules, Xeloda, Xgeva, Yervoy, Zaltrap, Zanosar, Zelboraf, Zevalin, Zinecard, Ziv-aflibercept, Zoladex, Zoledronic Acid, Zolinza, and Zometa.

Yet another aspect of the present invention relates to a method of inducing apoptosis of a cell, the method comprising contacting the cell with a peptidomimetic of the present invention under conditions effective to induce apoptosis of the cell.

Suitable cells according to this and all aspects of the present invention include, without limitation, mammalian cells. Preferably, the cells are human cells. In at least one embodiment, the cells are cancer cells. Suitable cancer cells include, e.g., anogenital cancer cells, including cervical cancer cells, vulvar cancer cells, vaginal cancer cells, penile cancer cells, anal cancer cells, as well as cancer cells of the head and neck, including HNSCC cells and oropharyngeal cancer cells. In at least one embodiment, the cells are infected with a high-risk HPV, as described above.

Another aspect of the present invention relates to a method of inducing decreasing survival and/or proliferation of a cell, the method comprising contacting the cell with a peptidomimetic of the present invention under conditions effective to decrease survival and/or proliferation of the cell.

Suitable cells include those noted above.

Another aspect of the present invention relates to a method of preventing or reversing inactivation of p53 in a cell, the method comprising contacting the cell with a peptidomimetic of the present invention under conditions effective to prevent or reverse inactivation of p53 in a cell.

Suitable cells include those noted above.

Yet another aspect of the present invention relates to a method of inhibiting p300-mediated acetylation of a transcription factor in a cell, the method comprising contacting the cell with a peptidomimetic of the present invention under conditions effective to inhibit p300-mediated acetylation of the transcription factor in the cell.

Suitable transcription factors according to this aspect of the present invention include any transcription factor whose acetylation is mediated by p300. In at least one embodiment, the transcription factor is p53.

Suitable cells include those noted above.

In all aspects of the present invention directed to methods involving contacting a cell with one or more peptidomimetics, contacting can be carried out using methods that will be apparent to the skilled artisan, and can be done in vitro or in vivo.

One approach for delivering agents into cells involves the use of liposomes. Basically, this involves providing a liposome which includes agent(s) to be delivered, and then contacting the target cell, tissue, or organ with the liposomes under conditions effective for delivery of the agent into the cell, tissue, or organ.

This liposome delivery system can also be made to accumulate at a target organ, tissue, or cell via active targeting (e.g., by incorporating an antibody or hormone on the surface of the liposomal vehicle). This can be achieved according to known methods.

An alternative approach for delivery of protein- or polypeptide-containing agents (e.g., peptidomimetics of the present invention containing one or more protein or polypeptide side chains) involves the conjugation of the desired agent to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of agents involves preparation of chimeric agents according to U.S. Pat. No. 5,817,789 to Heartlein et al., which is hereby incorporated by reference in its entirety. The chimeric agent can include a ligand domain and the agent (e.g., a peptidomimetic of the invention). The ligand domain is specific for receptors located on a target cell. Thus, when the chimeric agent is delivered intravenously or otherwise introduced into blood or lymph, the chimeric agent will adsorb to the targeted cell, and the targeted cell will internalize the chimeric agent.

Peptidomimetics of the present invention may be delivered directly to the targeted cell/tissue/organ.

Additionally and/or alternatively, the peptidomimetics may be administered to a non-targeted area along with one or more agents that facilitate migration of the peptidomimetics to (and/or uptake by) a targeted tissue, organ, or cell. As will be apparent to one of ordinary skill in the art, the peptidomimetic itself can be modified to facilitate its transport to a target tissue, organ, or cell, including its transport across the blood-brain barrier; and/or to facilitate its uptake by a target cell (e.g., its transport across cell membranes).

In vivo administration can be accomplished either via systemic administration to the subject or via targeted administration to affected tissues, organs, and/or cells, as described above. Typically, the therapeutic agent (i.e., a peptidomimetic of the present invention) will be administered to a patient in a vehicle that delivers the therapeutic agent(s) to the target cell, tissue, or organ. Typically, the therapeutic agent will be administered as a pharmaceutical formulation, such as those described above.

Exemplary routes of administration include, without limitation, orally, topically, transdermally, parenterally, subcutaneously, intravenously, intramuscularly, intraperitoneally, intraventricularly, and intralesionally; by intratracheal inoculation, aspiration, airway instillation, aerosolization, nebulization, intranasal instillation, oral or nasogastric instillation, intraperitoneal injection, intravascular injection, intravenous injection, intra-arterial injection (such as via the pulmonary artery), intramuscular injection, and intrapleural instillation; by application to mucous membranes (such as that of the nose, throat, bronchial tubes, genitals, and/or anus); and by implantation of a sustained release vehicle.

For use as aerosols, a peptidomimetic of the present invention in solution or suspension may be packaged in a pressurized aerosol container together with suitable propellants, for example, hydrocarbon propellants like propane, butane, or isobutane with conventional adjuvants. The peptidomimetics of the present invention also may be administered in a non-pressurized form.

Exemplary delivery devices include, without limitation, nebulizers, atomizers, liposomes (including both active and passive drug delivery techniques) (Wang & Huang, "pH-Sensitive Immunoliposomes Mediate Target-cell-specific Delivery and Controlled Expression of a Foreign Gene in Mouse," *Proc. Nat'l Acad. Sci. USA* 84:7851-5 (1987); Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al.; Wolff et al., "The Use of Monoclonal Anti-Thy1 IgG1 for the Targeting of Liposomes to AKR-A Cells in Vitro and in Vivo," *Biochim. Biophys. Acta* 802:259-73 (1984), each of which is hereby incorporated by reference in its entirety), transdermal patches, implants, implantable or injectable protein depot compositions, and syringes. Other delivery systems which are known to those of skill in the art can also be employed to achieve the desired delivery of the peptidomimetic to the desired organ, tissue, or cells in vivo to effect this aspect of the present invention.

Contacting (including in vivo administration) can be carried out as frequently as required and for a duration that is suitable to provide the desired effect. For example, contacting can be carried out once or multiple times, and in vivo administration can be carried out with a single sustained-release dosage formulation or with multiple (e.g., daily) doses.

The amount to be administered will, of course, vary depending upon the particular conditions and treatment regimen. The amount/dose required to obtain the desired effect may vary depending on the agent, formulation, cell type, culture conditions (for ex vivo embodiments), the duration for which treatment is desired, and, for in vivo embodiments, the individual to whom the agent is administered.

Effective amounts can be determined empirically by those of skill in the art. For example, this may involve assays in which varying amounts of the peptidomimetic of the invention are administered to cells in culture and the concentration effective for obtaining the desired result is calculated. Determination of effective amounts for in vivo administration may also involve in vitro assays in which varying doses of agent are administered to cells in culture and the concentration of agent effective for achieving the desired result is determined in order to calculate the concentration required in vivo. Effective amounts may also be based on in vivo animal studies.

The present invention may be further illustrated by reference to the following examples.

EXAMPLES

Example 1

Materials and Methods: Cell Lines

UMSCC47 and UMSCC74A were obtained from Dr. Thomas Carey at the University of Michigan. UPCI:SCC090 was provided by Dr. Susanne Gollin at the University of Pittsburgh (White et al., "The Influence of Clinical and Demographic Risk Factors on the Establishment of Head and Neck Squamous Cell Carcinoma Cell Lines," *Oral Oncol.* 43(7):701-12 (2007), which is hereby incorporated by reference in its entirety). UMSCC47, UMSCC74A, and UPCI:SCC090 cells were grown in DMEM containing 10% FBS, 2 mM glutamine, 100 mg/mL streptomycin and 100 U/mL penicillin and maintained in a humidified atmosphere of 5% $CO_2$ at 37° C.

Example 2

Materials and Methods: Plasmid Construction and Transfection

The CH1 domain of p300 (nucleotides 332-417) was amplified by PCR (forward primer: 5'-GGATCCATGCCAGAGAAGCGCAAGCTCATCCAGC-3' (SEQ ID NO: 5); reverse primer: 5'-CTCGAGATCACCAGCATTTTTGAGGGGGAGACAC-3' (SEQ ID NO:6)) and inserted into pcDNA3.1 between the BamHI and XhoI restriction enzyme sites. UMSCC47, UMUPCI:SCC090, and UMSCC74A cells were transfected with pcDNA3.1/empty or pcDNA3.1/CH1 using Lipofectamine2000 (Invitrogen, Carlsbad, Calif.). Stable polyclonal populations were selected and maintained in the presence of G418 (Invitrogen).

Example 3

Materials and Methods: Western Blot

Whole cell lysates were mixed with Laemmli loading buffer, boiled, separated by SDS-PAGE, and transferred to a nitrocellulose membrane. Subsequently, immunoblot analyses were performed using antibodies specific to V5 (Invitrogen), p53 (sc-126, Santa Cruz Biotechnology, Santa Cruz, Calif.), or acetylated[K382]-p53 (2525, Cell Signaling Technology). The signal was developed using the SuperSignal Western Blotting Kit (Pierce, Rockford, Ill.).

Example 4

Materials and Methods: p53 Transcriptional Activity

Cells were transfected with 100 ng of Cignal p53 reporter (SABiosciences, Valencia, Calif.) using Lipofectamine 2000. Cignal p53 reporter contains tandem repeats of the p53 consensus transcriptional response element. After 48 hours, cells were washed with cold PBS, lysed in passive lysis buffer (Promega), and measured for Firefly/Renilla dual luciferase activities in a luminometer using the Dual- Light System (Applied Biosystems, Foster City, Calif.). Renilla luciferase activity was normalized to Firefly luciferase activity to control for transfection efficiency. A modification to the protocol was used for compound treatment. UMSCC47 cells were transfected with 100 ng of Cignal p53 reporter. After 24 hours, cells were treated with vehicle, CH1iB (10 µM), cis-platinum (10 µM), or combination of CH1iB (10 µM) and cis-platinum (10 µM) and measured for Firefly/Renilla dual luciferase activities 24 hours post-treatment.

Example 5

Materials and Methods: Quantitative Real-Time PCR

Cells were extracted for total RNA using the TRIzol® reagent (Invitrogen) or TaqMan PreAmp Cells-to-CT kit (Applied Biosystems). Expression of p300, p53, p21, miR-34a and miR-200c were determined using the Applied Biosystems 7900HT Fast Real-Time PCR System with validated TaqMan gene expression assays (Applied Biosystems). p53, p300, and p21 expression were normalized to GADPH and miR-34a and miR-200c expression were normalized to RNU44 using the $\Delta\Delta Ct$ method.

Example 6

Materials and Methods: Immunoprecipitation

Cells were lysed with NP buffer [50 mM Tris (pH 8.0), 150 mM NaCl, 0.5% deoxycholate, 0.1% SDS, and 1.0% NP-40] containing 1× Protease Inhibitor Cocktail (Roche, Switzerland) at 4° C. with gentle rocking for 15 min. The supernatant was pre-cleared to block nonspecific binding with 50 µL protein A/G Agarose beads (Pierce Biotechnology) that had been pre-washed with NP buffer before use. Equal amounts of anti-E6 antibody (Abcam), anti-p300 antibody (Millipore), or IgG antibody (Cell Signaling) were added to the respective samples. After 4 hours incubation at 4° C., 50 µL pre-washed protein A/G-agarose beads were added to each tube and immunoprecipitation was performed by rocking overnight at 4° C. The immunoprecipitated complexes were washed with NP buffer and then eluted using 2×SDS sample buffer. Eluted sample and 10% of input were resolved by SDS-PAGE for Western blot analysis with anti-E6, anti-p300, or anti-V5 antibodies.

Example 7

Materials and Methods: Cell Proliferation, Clonogenic Survival, and Apoptosis

Cell proliferation was assessed using the MTT reagent (Roche Molecular Biochemicals, Nutley, N.J.) to detect metabolic active cells. Absorbance was measured at 570 nm in the Spectra Max 190 ELISA reader (Molecular Devices, Sunnyvale, Calif.) after overnight incubation. For clonogenic survival, 200 cells per well were plated in complete growth media and allowed to grow until visible colonies were formed (14 days). Cell colonies were fixed with cold methanol, stained with 0.25% crystal violet in 25% methanol, washed, and air dried. For apoptosis, cells were harvested, washed with cold PBS, and co-stained with Annexin V and propidium iodide according to the manufacturer's protocol (ApoAlert Annexin V-FITC Apoptosis Kit; Clontech). Apoptotic cells were analyzed using BD FACS Calibur (BD Biosciences Corporation, Franklin Lakes, N.J.) at The Ohio State University Comprehensive Cancer Center Analytical Cytometry Core.

Example 8

Materials and Methods: Tumor Incidence and Growth in Athymic Nude Mice

UMSCC47/empty and UMSCC47/CH1 cells were suspended in 50:50 DMEM:Matrigel and implanted subcutaneously into the left and right flanks of 6-week old athymic nude mice (8 mice/group), respectively. After 3 weeks, tumors were measured once a week using a digital caliper and tumor volumes were calculated using the formula d1×d2×d3×0.5236, where "d" represents the three orthogonal diameters. Tumor growth and incidence were monitored for 49 days following tumor cell implantation.

Example 9

Materials and Methods: ALDH and CD44

Cells were assessed for ALDH activity using the ALDEFLUOR kit according to the manufacturer's protocol (Stem Cell Technologies, British Columbia, Canada). Cells were suspended in ALDEFLUOR assay buffer containing ALDH substrate (bidipy-aminoacetaldehyde, 1 µM per $1 \times 10^6$ cells) and incubated for 40 minutes at 37° C. For each experiment, a sample of cells was incubated with 50 mM of diethylaminobenzaldehyde (DEAB), a specific ALDH inhibitor, to serve as the negative control. For CD44 expression, cells were harvested and resuspended in incubation buffer with PE-CD44 antibody (Abcam) or mouse PE-IgG (Abcam) for 50 minutes on ice. Suspensions were centrifuged at 300×g for 5 minutes at 4° C. and resuspend in 0.5 mL of 1% paraformaldehyde solution for analysis. Fluorescence activated cell sorting (FACS) analyses were performed using BD FACS Calibur at The Ohio State University Comprehensive Cancer Center Analytical Cytometry Core.

Example 10

Materials and Methods: Tumorsphere Formation

Cells were harvested and seeded in a serum-free defined medium consisting of KSF medium supplemented with epidermal growth factor, basic fibroblast growth factor, insulin, and hydrocortisone in low-attachment plates (Corning Incorporated, Corning, N.Y.) for tumorspheres. Tumorsphere formation efficiency was calculated as the number of tumorspheres (≥50 µm in diameter) formed in 7 days divided by the original number of cells seeded. Tumorsphere diameter was measured using NIS-Elements software.

Example 11

Materials and Methods: Tumor Incidence with a Single Tumorsphere

Tumorsphere derived from UMSCC47 cells were generated and measured using NIS-Elements software. A single tumorsphere (60-80 µm in diameter) was suspended in 50:50 KSF:Matrigel and implanted subcutaneously into the flank of 6-week old NOD/SCID mice (n=11). In a separate set of animals, parental UMSCC47 cells ($1 \times 10^3$) were suspended in 50:50 DMEM:Matrigel and implanted subcutaneously into the flank of 6-week old NOD/SCID mice (n=10). Tumor incidence was monitored for 180 days following tumorsphere or tumor cell implantation.

Example 12

Materials and Methods: Synthesis of Inhibitors

Synthetic helices were synthesized as previously described (Henchey et al., "Inhibition of Hypoxia Inducible Factor 1-Transcription Coactivator Interaction by a Hydrogen Bond Surrogate Alpha-Helix," *J. Am. Chem. Soc.* 132(3):941-43 (2010); Patgiri et al., "Solid-Phase Synthesis of Short Alpha-Helices Stabilized by the Hydrogen Bond Surrogate Approach," *Nat. Protoc.* 5(11):1857-65 (2010), which are hereby incorporated by reference in their entirety). Compounds were purified by reverse-phase HPLC (see FIGS. 1A-C) and characterized by ESI-MS, as shown in Table 1 below.

TABLE 1

Mass Spectroscopic Characterization of CH1 Inhibitors

| COMPOUND | SEQUENCE[A] | SEQ ID NO: | CALCULATED [M + H]$^+$ | OBSERVED [M + H]$^+$ |
| --- | --- | --- | --- | --- |
| CH1IA | XTAA*DCEYNAR | 7 | 1206.5 | 1206.4 |
| CH1IB | XELA*RALDQ-NH$_2$ | 8 | 1008.5 | 1008.5 |
| CH1IB-MUT | XELA*RAADQ-NH$_2$ | 9 | 966.5 | 966.5 |

X denotes 4-pentenoic acid;
[A]*= N-allylalanine.

Example 13

Materials and Methods: Statistical Analysis

Data were analyzed by two-tailed Student's t-test. P-values <0.05 were considered significant.

Example 14

Exogenous CH1 Reactivates p53 by Blocking the Association Between HPV16 E6 and p300

High-risk HPV E6 was reported to associate with p300 to inhibit p300-mediated p53 acetylation (Zimmermann et al., "The Human Papillomavirus Type 16 E6 Oncoprotein Can Down-Regulate p53 Activity by Targeting the Transcriptional Coactivator CBP/p300," *J. Virol.* 73(8):6209-19 (1999); Patel et al., "The E6 Protein of Human Papillomavirus Type 16 Binds to and Inhibits Co-Activation by CBP and p300," *EMBO J.* 18(18):5061-72 (1999); Thomas & Chiang, "E6 Oncoprotein Represses p53-Dependent Gene Activation Via Inhibition of Protein Acetylation Independently of Inducing p53 Degradation," *Mol. Cell* 17(2):251-64 (2005), which are hereby incorporated by reference in their entirety). Acetylation is a critical regulatory mechanism to control p53 stability and transcriptional activity (Zimmermann et al., "The Human Papillomavirus Type 16 E6 Oncoprotein Can Down-Regulate p53 Activity by Targeting the Transcriptional Coactivator CBP/p300," *J. Virol.* 73(8):6209-19 (1999); Patel et al., "The E6 Protein of Human Papillomavirus Type 16 Binds to and Inhibits Co-Activation by CBP and p300," *EMBO J.* 18(18):5061-72 (1999); Thomas & Chiang, "E6 Oncoprotein Represses p53-Dependent Gene Activation Via Inhibition of Protein Acetylation Independently of Inducing p53 Degradation," *Mol. Cell* 17(2):251-64 (2005); Ito et al., "MDM2-HDAC1-Mediated Deacetylation of p53 Is Required for Its Degradation," EMBO J. 21(22):6236-45 (2002); Li et al., "Acetylation of p53 Inhibits Its Ubiquitination by Mdm2," *J. Biol. Chem.* 277(52):50607-11 (2002), which are hereby incorporated by reference in their entirety). Therefore, targeting the E6-p300 interaction may be a novel approach to reactivate p53 in HPV-positive HNSCC. Published work showed that high-risk HPV E6 binds to the CH1, CH3, and C-terminal domain of p300 (Patel et al., "The E6 Protein of Human Papillomavirus Type 16 Binds to and Inhibits Co-Activation by CBP and p300," *EMBO J.* 18(18):5061-72 (1999), which is hereby incorporated by reference in its entirety). Thus, we determined if targeting one of the contact sites, the CH1 domain, is a tractable approach to block the association between E6 and p300 and reactivate p53. As shown in FIG. 2A, exogenous CH1 squelched E6 to reduce the association between E6 and p300 in UMSCC47 and UPCI:SCC090, two HPV16-positive HNSCC cell lines. An accumulation of total p53 and an increase in acetylated p53 was revealed in CH1 overexpressing UMSCC47 (UMSCC47/CH1) and UPCI:SCC090 (SCC090/CH1) cells (FIG. 2B). p53 transcription activity was elevated by 85% (P<0.01) and 50% (P<0.01) in UMSCC47/CH1 and UPCI:SCC090/CH1 cells, respectively (FIG. 2C). Overexpression of CH1 had no effect on p53 and p300 expression but enhanced the expression of three well-recognized p53 targets. p21, miR-34a, and miR-200c expression were increased by 114%, 323%, and 80% in UMSCC47/CH1 cells (P<0.01) and 39%, 134%, and 49% in UPCI:SCC090/CH1 cells (P<0.01), respectively (FIG. 2E). These results demonstrate that blocking the E6-p300 interaction is an efficient approach to reactive p53, through p53 accumulation and acetylation, in HPV-positive HNSCC.

Example 15

Exogenous CH1 Has a Pleiotropic Anti-Tumor Effect in HPV16-Positive HNSCC

We determined if reactivation of p53 is sufficient to promote an anti-tumor response in HPV-positive HNSCC cells. Cell proliferation and clonogenic survival were reduced by 20% and 55% in UMSCC47/CH1 cells and 11% and 58% in UMUPCI:SCC090/CH1 cells, respectively (FIGS. 3A and 3B). Moreover, CH1 overexpression increased apoptosis by 60% in UMSCC47 cells and 27% in UPCI:SCC090 cells (FIG. 3C). A similar response in cell proliferation, clonogenic survival, and apoptosis was observed for empty vector-transfected UMSCC47 and UPCI:SCC090 cells treated with single agent cis-platinum (10 µM). UMSCC47/CH1 and UPCI:SCC090/CH1 cells were dramatically more responsive to cis-platinum (10 μM) than UMSCC47/empty and UPCI:SCC090/empty cells. The combination of CH1 overexpression and cis-platinum treatment reduced cell proliferation by 46% and 23%, reduced clonogenic survival by 85% and 77%, and enhanced apoptosis by 194% and 157% in UMSCC47 and UPCI:SCC090, respectively (P<0.01). Our results indicate that reactivation of p53 was sufficient to promote a broad anti-tumor response and furthermore, enhanced the efficacy of cis-platinum in HPV-positive HNSCC cells.

Next, we determined if CH1 overexpression modulates the in vivo tumorigenicity of HPV-positive HNSCC cells. Two different dilutions, $3 \times 10^5$ or $3 \times 10^4$, of UMSCC47/empty and UMSCC47/CH1 cells were implanted in the flanks of athymic nude mice (FIG. 3D). At a dilution of $3 \times 10^5$ cells, tumor incidence was the same between UMSCC47/empty and UMSCC47/CH1 cells however a difference (P<0.01, n=6) in tumor volume was observed. Mean tumor volume was 142 mm$^3$ for UMSCC47/empty and 67 mm$^3$ for UMSCC47/CH1 (FIG. 3E). Interestingly, at a dilution of $3 \times 10^4$ cells, tumor incidence was 50% (4/8) for UMSCC47/empty but 0% (0/8) for UMSCC47/CH1 (P<0.02). This observation suggests that the CIC population may be compromised in HPV16-positive HNSCC following p53 reactivation. CICs are a sub-set of cancer cells within the tumor with the exclusive capacity to divide and expand the CIC pool or to differentiate into heterogeneous non-tumorigenic cells that constitute the bulk of the tumor. CICs are postulated to be the unique cells responsible for disease recurrence and/or metastasis. Therefore, elimination of CICs may be essential to optimally manage cancer patients. ALDH and CD44 are two markers used to identify the CIC population in HNSCC (Prince et al., "Identification of a Subpopulation of Cells With Cancer Stem Cell Properties in Head and Neck Squamous Cell Carcinoma," *Proc. Nat'l Acad. Sci. U.S.A.* 104(3):973-78 (2007); Clay et al., "Single-Marker Identification of Head and Neck Squamous Cell Carcinoma Cancer Stem Cells With Aldehyde Dehydrogenase," *Head Neck* 32(9): 1195-201 (2010); Chen et al., "Aldehyde Dehydrogenase 1 Is a Putative Marker for Cancer Stem Cells in Head and Neck Squamous Cancer," *Biochem. Biophys. Res. Commun.* 385(3):307-13 (2009), which are hereby incorporated by reference in their entirety). As shown in FIG. 3F, CH1 overexpression reduced the ALDH$^{high}$ population by 46% (P<0.01) and CD44$^{high}$ population by 31% in UMSCC47 cells (P<0.01). Moreover, FACS analysis showed that CD44 levels were reduced by 33% in UMSCC47/CH1 cells compared to UMSCC47/empty cells. Tumorsphere formation is an in vitro assay to assess the CIC population. Overexpression of CH1 in UMSCC47 cells inhibited tumorsphere formation efficiency by 42% (P<0.01) and reduced tumorsphere diameter by 25% (P<0.01) (FIG. 3G). To confirm the tumor initiating potential of tumorspheres, NOD/SCID mice were implanted with a single tumorsphere (mean diameter of 60-80 μm with ~100 cells) and monitored for tumor incidence over a 6 month period (FIG. 3H). Mice implanted with a single tumorsphere had a tumor incidence rate of 55% (6/11). In contrast, all the mice implanted with $1 \times 10^3$ UMSCC47 cells failed to develop tumors over a 6 month period. Our work demonstrate that reactivation of p53 suppress the in vivo tumorigenicity of HPV-positive HNSCC, in part through a reduction in the CIC population.

Example 16

Exogenous CH1 Has a Pleiotropic Anti-Tumor Effect in HPV-Negative HNSCC

There is evidence that p300 is indispensable for MDM2-mediated p53 degradation (Grossman et al., "p300/MDM2 Complexes Participate in MDM2-Mediated p53 Degradation," *Mol. Cell* 2(4):405-15 (1998); Kobet et al., "MDM2 Inhibits p300-Mediated p53 Acetylation and Activation by Forming a Ternary Complex With the Two Proteins," *Proc. Nat'l Acad. Sci. U.S.A.* 97(23):12547-52 (2000), which are hereby incorporated by reference in their entirety). MDM2 was shown to bind to the CH1 domain of p300 and overexpression of CH1 was sufficient to enhance p53 stability in p53 wildtype human osteosarcoma U2OS cells (Grossman et al., "p300/MDM2 Complexes Participate in MDM2-Mediated p53 Degradation," *Mol. Cell* 2(4):405-15 (1998); Kobet et al., "MDM2 Inhibits p300-Mediated p53 Acetylation and Activation by Forming a Ternary Complex With the Two Proteins," *Proc. Nat'l Acad. Sci. U.S.A.* 97(23): 12547-52 (2000), which are hereby incorporated by reference in their entirety). In line with these observations, ectopic expression of CH1 increased total and acetylated p53 in p53 wildtype, HPV-negative UMSCC74A HNSCC cells (FIG. 4A). p53 transcription activity was elevated by 68% (P<0.05) in UMSCC74A/CH1 compared to UMSCC74A/empty cells (FIG. 4B). As shown in FIG. 4C, the interaction between p300 and MDM2 in UMSCC74A cells was disrupted with the introduction of CH1. Overexpression of CH1 inhibited cell proliferation (48%, P<0.01) and clonogenic survival (70%, P<0.01), and increased apoptosis (95%, P<0.05) in UMSCC74A cells. In addition, UMSCC74A/CH1 cells were more responsive to the anti-tumor effects of cis-platinum (10 μM) than UMSCC74A/empty cells. Our work demonstrates that exogenous CH1 blocked p300-MDM2 interaction, enhanced p53 activity, and promoted a broad anti-tumor response in HPV-negative HNSCC cells.

Example 17

CH1iB, a Small Molecule CH1 Inhibitor, Preferentially Reactivates p53 in HPV16-Positive HNSCC Our results showed that exogenous CH1 reactivated p53 in HPV-positive and HPV-negative HNSCC. We determined if small molecule CH1 ligands can function as competitive inhibitors to mask the E6 and MDM2 binding sites on p$^{300}$ and block the E6-p300 and MDM2-p300 association. HIF-1α recruits and binds to the CH1 domain of p300 to facilitate HIF-1α-mediated transcription of target genes (Dames et al., "Structural Basis for Hif-1 Alpha/CBP Recognition in the Cellular Hypoxic Response," *Proc. Nat'l Acad. Sci. U.S.A.* 99(8):5271-76 (2002); Freedman et al., "Structural Basis for Recruitment of CBP/p300 by Hypoxia-Inducible Factor-1 Alpha," *Proc. Nat'l Acad. Sci. U.S.A.* 99(8):5367-72 (2002), which are hereby incorporated by reference in their entirety). A stabilized α-helical mimic, constrained by the hydrogen bond surrogate methodology (Patgiri et al., "A Hydrogen Bond Surrogate Approach for Stabilization of Short Peptide Sequences in Alpha-Helical Conformation," *Acc. Chem. Res.* 41(10):1289-300 (2008), which is hereby incorporated by reference in its entirety), of HIF-1α (CH1iA) was reported to function as a CH1 inhibitor and compete with endogenous HIF-1α for p300 resulting in a reduction in HIF-1α-mediated transcription of vascular endothelial growth factor (Henchey et al., "Inhibition of Hypoxia Inducible Factor 1-Transcription Coactivator Interaction by a Hydrogen Bond Surrogate Alpha-Helix," *J. Am. Chem. Soc.* 132(3):941-43 (2010), which is hereby incorporated by reference in its entirety). The CH1 domain of p300 features multiple binding sites for individual α-helices (Dames et al., "Structural Basis for Hif-1 Alpha/CBP Recognition in the Cellular Hypoxic Response," *Proc. Nat'l Acad. Sci. U.S.A.* 99(8):5271-76 (2002); Freedman et al., "Structural Basis for Recruitment of CBP/p300 by Hypoxia-Inducible Factor-1 Alpha," *Proc. Nat'l Acad. Sci. U.S.A.* 99(8):5367-72 (2002), which are hereby incorporated by reference in their entirety) suggesting that targeting a distinct CH1-binding partner may be a possibility. We tested the ability of synthetic helices that target binding site A and site B in CH1 in HPV-negative and HPV-positive HNSCC (FIG. 5B). CH1iA and CH1iB did not modulate p53 activity and levels in UMSCC74A, a HPV-negative, p53 wildtype HNSCC cell line (FIGS. 5C and 5D). Expression of p300, p53, and p53-regulated genes were unchanged following CH1iA or CH1iB treatment in UMSCC74A cells (FIG. 5E). In HPV-positive UMSCC47 cells, CH1iA had no effect whereas CH1iB enhanced p53 activity (71% increase, P<0.01), p53 accumulation, and acetylated p53 levels. A modest but significant increase in p21, miR-34a, and miR-200c expression was shown following CH1iB treatment (FIG. 5E). Furthermore, the association between E6 and p300 was reduced with CH1iB but not with CH1iA treatment in HPV-positive HNSCC cells (FIG. 5F). These results reveal that the critical binding contacts between E6 and CH1 are located within or in proximity to binding site B of the CH1 domain. In FIG. 5G, CH1iA was inactive but CH1iB inhibited the proliferation of HPV-positive UMSCC47 cells as single-agent and potentiated the anti-proliferative efficacy of cis-platinum. CH1iA and CH1iB had no effect and did not augment the efficacy of cis-platinum on the proliferation of HPV-negative UMSCC74A cells and human normal IMR90 fibroblasts. Taken together, our work demonstrates that targeting binding site B in CH1 with CH1iB preferentially reactivates p53 in HPV-positive HNSCC cells by disrupting the association between E6 and p300.

Example 18

CH1iB Potentiates the Efficacy of cis-Platinum in HPV16-Positive HNSCC

Our results showed that introduction of CH1 potentiated the effects of cis-platinum on cell proliferation, clonogenic survival, and apoptosis in HPV-positive HNSCC. In addition, CH1iB enhanced the anti-proliferative action of cis-platinum in UMSCC47 cells. As shown in FIGS. 6A-F, CH1iB potentiated the effect of cis-platinum on p53 accumulation, acetylation, and activity. Expression of p21, miR-34a, and miR-200c was dramatically higher (P<0.01) with the combination treatment than with either single-agent treatment (FIG. 6C). Compared to vehicle-treated UMSCC47 cells, CH1iB reduced clonogenic survival by 35% and tumorsphere formation by 20%, and enhanced apoptosis by 353% (P<0.01). Furthermore, the combination regimen was highly active and almost completely ablated the clonogenic survival (91% inhibition, P<0.01) of HPV16-positive HNSCC cells. Apoptosis induced by the combination treatment was increased by 984% (P<0.01) and 443% (P<0.01) compared to CH1iB and cis-platinum, respectively (FIG. 6D). In addition, tumorsphere formation was suppressed by a greater extent with the combination regimen than single-agent CH1iB or cis-platinum (FIG. 6F). CH1iB-mut, a designed specificity control for CH1iB in which one energetically important leucine residue is mutated to alanine, showed a minimal but significant increase (14% increase, P<0.05) in p53 activity but, importantly, had no effect as single-agent or in combination with cis-platinum to inhibit cell proliferation in UMSCC47 cells (FIGS. 7A-B).

These results indicate that CH1iB, a CH1 inhibitor, potentiates the anti-tumor activity of cis-platinum in HPV-positive HNSCC.

Discussion of Examples 1-18

High-risk HPV is recognized as an etiological agent for the pathogenesis of anogenital and head and neck squamous cell carcinomas. HPV E6 inactivates p53 through two distinct and independent pathways. It is well recognized that E6 complexes with E6AP to form an active E3-ubiquitin ligase to target p53 for proteasome-dependent proteolysis (Talis et al., "The Role of E6AP in the Regulation of p53 Protein Levels in Human Papillomavirus (HPV)-Positive and HPV-Negative Cells," *J. Biol. Chem.* 273(11):6439-45 (1998), which is hereby incorporated by reference in its entirety). A second but much more under-appreciated mechanism is that E6 associates with the p300-p53 complex to block p300-mediated acetylation and activation of p53 (Thomas & Chiang, "E6 Oncoprotein Represses p53-Dependent Gene Activation Via Inhibition of Protein Acetylation Independently of Inducing p53 Degradation," *Mol. Cell* 17(2):251-64 (2005), which is hereby incorporated by reference in its entirety). p300 acetylates p53 at multiple lysine residues, including K370, 372, 381, and 382 (Gu & Roeder, "Activation of p53 Sequence-Specific DNA Binding by Acetylation of the p53 C-Terminal Domain," *Cell* 90(4):595-606 (1997), which is hereby incorporated by reference in its entirety). Acetylation was shown to control p53 function through multiple mechanisms, including an increase in protein stability, tetramerization, DNA binding, and co-activator recruitment (Thomas & Chiang, "E6 Oncoprotein Represses p53-Dependent Gene Activation Via Inhibition of Protein Acetylation Independently of Inducing p53 Degradation," *Mol. Cell* 17(2):251-64 (2005); Li et al., "Acetylation of p53 Inhibits Its Ubiquitination by Mdm2," *J. Biol. Chem.* 277(52):50607-11 (2002); Gu & Roeder, "Activation of p53 Sequence-Specific DNA Binding by Acetylation of the p53 C-Terminal Domain," *Cell* 90(4):595-606 (1997), which are hereby incorporated by reference in their entirety).

Several groups reported that reactivation of p53 is achievable in HPV-positive cervical carcinomas using different strategies to reduce E6 or E6AP levels (Beerheide et al., "Potential Drugs Against Cervical Cancer: Zinc-Ejecting Inhibitors of the Human Papillomavirus Type 16 E6 Oncoprotein," *J. Nat'l Cancer Inst.* 91(14): 1211-20 (1999); Beerheide et al., "Inactivation of the Human Papillomavirus-16 E6 Oncoprotein by Organic Disulfides," *Bioorg. Med. Chem.* 8(11):2549-60 (2000); Courtete et al., "Suppression of Cervical Carcinoma Cell Growth by Intracytoplasmic Codelivery of Anti-Oncoprotein E6 Antibody and Small Interfering RNA," *Mol. Cancer. Ther.* 6(6):1728-35 (2007); Beer-Romero et al., "Antisense Targeting of E6AP Elevates p53 in HPV-Infected Cells but Not in Normal Cells," *Oncogene* 14(5):595-602 (1997); Koivusalo et al., "Activation of p53 in Cervical Cancer Cells by Human Papillomavirus E6 RNA Interference Is Transient, but Can Be Sustained by Inhibiting Endogenous Nuclear Export-Dependent p53 Antagonists," *Cancer Res.* 66(24):11817-24 (2006); Zhao et al., "Rescue of p53 Function by Small-Molecule RITA in Cervical Carcinoma by Blocking E6-Mediated Degradation," *Cancer Res.* 70(8):3372-81 (2010), which are hereby incorporated by reference in their entirety). Treatment with E6AP anti-sense oligonucleotides accumulated p53 but did not promote apoptosis (Beer-Romero et al., "Antisense Targeting of E6AP Elevates p53 in HPV-Infected Cells but Not in Normal Cells," *Oncogene* 14(5):595-602 (1997), which is hereby incorporated by reference in its entirety). These authors suggest that a threshold level of p53 levels may be required for p53-mediated apoptosis. An alternate explanation is the ablation of E6AP may be inefficient to reactivate p53 since E6 is still available to suppress p300-mediated acetylation and activation of p53. Co-delivery of a HPV16 E6 antibody and E6 siRNA enhanced p53 levels and decreased clonogenic survival; however, an apoptotic response was not detected (Courtete et al., "Suppression of Cervical Carcinoma Cell Growth by Intracytoplasmic Codelivery of Anti-Oncoprotein E6 Antibody and Small Interfering RNA," *Mol. Cancer Ther.* 6(6):1728-35 (2007), which is hereby incorporated by reference in its entirety). An interesting study showed that siRNA-mediated ablation of E6 results in a transient increase in p53 protein and activity despite a sustained E6 knockdown suggesting that a compensatory p53 degradation and/or inactivation mechanism is quickly triggered in HPV-positive cervical carcinomas cells under these experimental conditions (Koivusalo et al., "Activation of p53 in Cervical Cancer Cells by Human Papillomavirus E6 RNA Interference Is Transient, but Can Be Sustained by Inhibiting Endogenous Nuclear Export-Dependent p53 Antagonists," *Cancer Res.* 66(24):11817-24 (2006), which is hereby incorporated by reference in its entirety).

Disruption of E6-p300 association is an approach that has not be utilized to reactivate p53 in HPV-positive carcinomas. Restoration of p300-mediated acetylation of p53 may be an ideal strategy since acetylation controls p53 function through multiple mechanisms, including stability and transcriptional activation. Our results with stable CH1 overexpressing HNSCC cells indicate that targeting the E6-p300 interaction is sufficient to maintain elevated p53 accumulation, acetylation, and activity ad infinitum. Exogenous CH1 inhibits cell proliferation and clonogenic survival and enhances apoptosis in HPV-positive HNSCC. Importantly, the in vivo tumorigenicity of UMSCC47/CH1 cells is severely compromised in part through a reduction in the CIC population. Thus, our data showed that restoration of p300-mediated p53 acetylation induces a sustained p53 reactivation and anti-tumor response in HPV-positive HNSCC.

It was reported that p300 functions as a scaffold for MDM2 and p53 to facilitate MDM2-mediated degradation of p53 (Grossman et al., "p300/MDM2 Complexes Participate in MDM2-Mediated p53 Degradation," *Mol. Cell* 2(4): 405-15 (1998), which is hereby incorporated by reference in its entirety). Overexpression of the CH1 domain of p300 enhanced p53 accumulation in human osteosarcoma U20S cells presumably by blocking the physical interaction between p300 and MDM2 (Grossman et al., "p300/MDM2 Complexes Participate in MDM2-Mediated p53 Degradation," *Mol. Cell* 2(4):405-15 (1998), which is hereby incorporated by reference in its entirety). Also, binding of MDM2 to the p300-p53 complex blocked p300-mediated acetylation and activation of p53 (Kobet et al., "MDM2 Inhibits p300-Mediated p53 Acetylation and Activation by Forming a Ternary Complex With the Two Proteins," *Proc. Nat'l Acad. Sci. U.S.A.* 97(23):12547-52 (2000), which is hereby incorporated by reference in its entirety). These results indicate that the MDM2-p300-p53 complex is intimately involved in p53 turnover, acetylation, and activation. In direct support, our results showed that exogenous CH1 disrupts MDM2-p300 association and increases p53 levels and activity in p53 wildtype, HPV-negative UMSCC74A HNSCC cells. In addition, CH1 overexpression sensitized UMSCC74A cells to the anti-tumor efficacy of cis-platinum. These results demonstrate that targeting the CH1 domain of p300 may be a tractable approach to enhance p53 activity in HNSCC cells with wildtype p53, regardless of HPV status, albeit through distinct mechanisms. CH1iB, but not CH1iA, blocked E6-p300 association and reactivated p53 in HPV-positive HNSCC indicating that binding site B in the CH1 domain contains the critical contacts for E6 and p300 interaction. Interestingly, selective targeting of the CH1 domain with CH1iA and CH1iB did not enhance p53 accumulation and activity in UMSCC74A cells. The preferential activity of CH1iB for HPV-positive HNSCC over HPV-negative HNSCC suggests that the CH1-binding interface for E6 may be distinct from the CH1-binding interface for MDM2. Another possibility is that MDM2 may have a tighter binding association for p300 than E6 and thus, CH1iB and CH1iA were unable to successfully compete against MDM2 for p300 binding. In any event, our work reveals that CH1iB preferentially reactivates p53 activity in HPV-positive HNSCC cells providing initial evidence that discrete chemical targeting of the CH1 domain of p300 can be realized.

The role of p53 in normal stem cell regulation is established and is beginning to emerge for CICs. Inhibition of p53 dramatically enhanced the transformation efficiency of differentiated cells into induced pluripotent stem cells (Hong et al., "Suppression of Induced Pluripotent Stem Cell Generation by the p53-p21 Pathway," *Nature* 460(7259): 1132-35 (2009); Kawamura et al., "Linking the p53 Tumour Suppressor Pathway to Somatic Cell Reprogramming," *Nature* 460(7259): 1140-44 (2009); Utikal et al., "Immortalization Eliminates a Roadblock During Cellular Reprogramming Into iPS Cells," *Nature* 460(7259):1145-48 (2009), which are hereby incorporated by reference in their entirety). Loss of p53 favored self-renewal, symmetric cell division, of mammary stem cells resulting in an expansion of the stem cell population (Cicalese et al., "The Tumor Suppressor p53 Regulates Polarity of Self-Renewing Divisions in Mammary Stem Cells," *Cell* 138(6): 1083-95 (2009), which is hereby incorporated by reference in its entirety). Two p53 targets, miR-34a and p21, were shown to contribute to p53 repression of induced pluripotent stem cells (Hong et al., "Suppression of Induced Pluripotent Stem Cell Generation by the p53-p21 Pathway," *Nature* 460(7259):1132-35 (2009); Kawamura et al., "Linking the p53 Tumour Suppressor Pathway to Somatic Cell Reprogramming," *Nature* 460 (7259): 1140-44 (2009); Choi et al., "miR-34 miRNAs Provide a Barrier for Somatic Cell Reprogramming," *Nat. Cell Biol.* 13(11): 1353-60 (2011), which are hereby incorporated by reference in their entirety). Additionally, miR-34a blocked prostate CIC expansion (Liu et al., "The MicroRNA miR-34a Inhibits Prostate Cancer Stem Cells and Metastasis by Directly Repressing CD44," *Nat. Med.* 17(2): 211-15 (2011), which is hereby incorporated by reference in its entirety). Loss of p53 in mammary epithelial cells led to reduced miR-200c expression resulting in an increase in EMT-associated CIC population (Chang et al., "p53 Regulates Epithelial-Mesenchymal Transition and Stem Cell Properties Through Modulating miRNAs," *Nat. Cell Biol.* 13(3):317-23 (2011), which is hereby incorporated by reference in its entirety). Our results are in line with these studies and further support the link between p53 and CICs. We show that reactivation of p53 in HPV-positive HNSCC increase the expression of p21, miR-34a, and miR-200c and reduce the CIC population. These observations suggest that the p53-p21/miR-34a/miR-200c circuitry to limit normal stem cell expansion, either through reprogramming or self-renewal, can be triggered in HPV-positive HNSCC to block CIC expansion through p53 reactivation. It is unclear at this time whether the reduction in the CIC population is due to a shift in favor of asymmetric CIC division and/or differentiation of CICs. Additional work will be necessary to address this question and to dissect the contributions of p21, miR-34a, and miR-200c in controlling the CIC population.

High-dose cis-platinum-based therapy is the standard of care for definitive treatment of HPV-positive cancers, but is associated with high toxicities and difficult for patients to tolerate (Pan et al., "Pharmacotherapy of Head and Neck Squamous Cell Carcinoma," Expert Opin. Pharmacother. 10(14):2291-302 (2009), which is hereby incorporated by reference in its entirety). Treatment-associated toxicities from high-dose cis-platinum-based therapy are a major concern and have prompted considerable discussion whether alternate treatment or de-intensification of treatment should be offered for the HPV-positive HNSCC population. Considering there are limited clinical options for HPV-positive HNSCC at this time, alternative treatment strategies are critically needed. We showed that CH1iB, a CH1 inhibitor, reactivates p53 in HPV-positive HNSCC. Single-agent CH1iB exhibits broad anti-cancer activity to suppress cell proliferation and clonogenic survival and enhance apoptosis in UMSCC47 and UPCI:SCC090 cells. Interestingly, CH1iB potentiates cis-platinum-mediated p53 activity and anti-tumor efficacy. HPV-positive HNSCC cells are almost completely eliminated following treatment with the combination of CH1iB and cis-platinum. Based on these results, we speculate that fewer cycles or a tapered dose of cis-platinum may be sufficient in the presence of a CH1 inhibitor to effectively manage HPV-positive HNSCC patients with a better toxicity profile. Our data strongly supports further development of CH1 inhibitors as p53 reactivation therapeutics for HPV-positive HNSCC.

The E6 viral protein is conserved across HPV serotypes (E.g., Scheffner et al., "The E6 Oncoprotein Encoded by Human Papillomavirus Types 16 and 18 Promotes the Degradation of p53," Cell 63(6):1129-36 (1990), which is hereby incorporated by reference in its entirety). Thus, our results reveal that targeting the E6-p300 association is a novel approach to reactivate p53 in HPV-positive cancer cells, such as HNSCC. CH1iB, a small molecule CH1 inhibitor, reactivates p53 and potentiates the anti-tumor activity of cis-platinum in HPV-positive HNSCC cells. Our work indicates that CH1 domain inhibitors, like those described herein, represent a novel class of p53 reactivation therapeutics for HPV-positive cancers.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A peptidomimetic, wherein the peptidomimetic is selected from the group consisting of:

(i) a compound of Formula Ia, Ib, Ic, Id, Ie, or If:

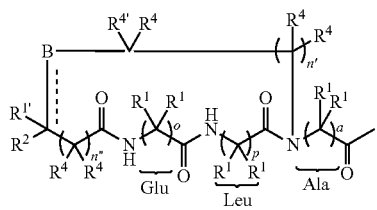

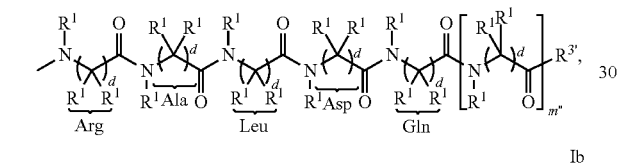

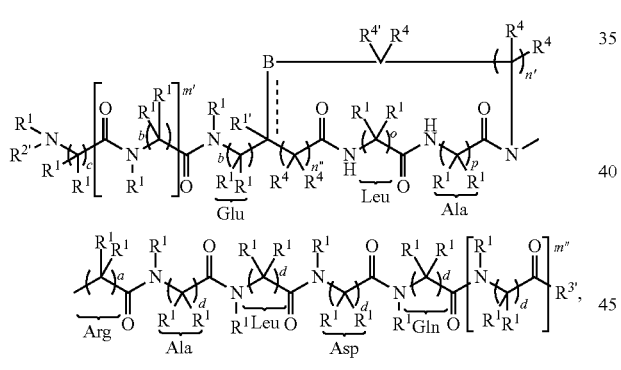

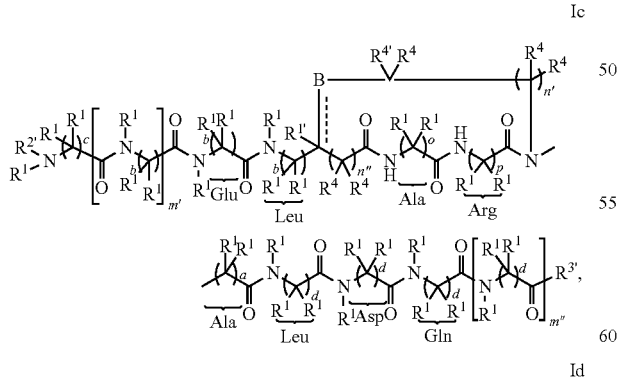

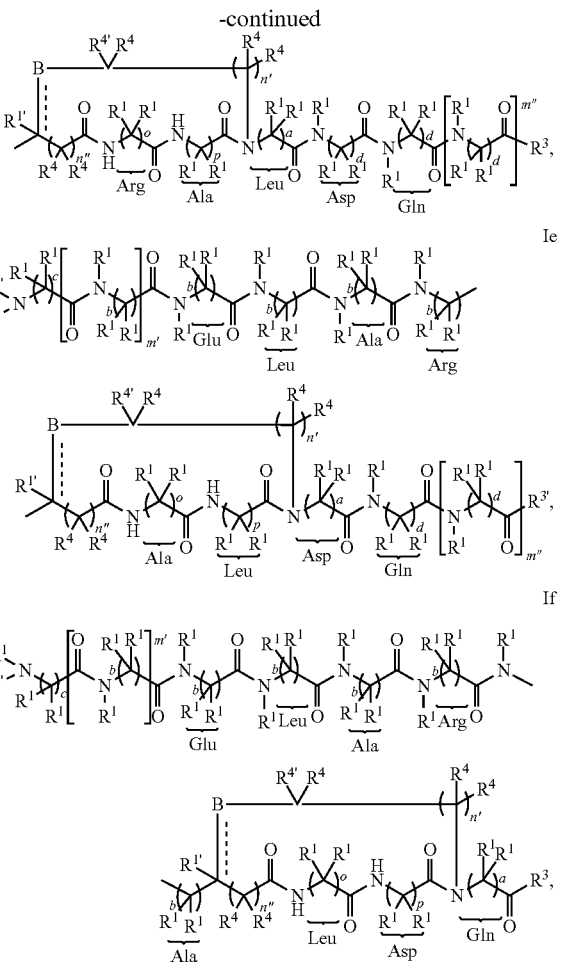

wherein:
- B is $C(R^1)(R^{1'})$, O, S, or $NR^1$;
- ------ is a double bond and each $R^{1'}$ is absent; or
- ------ is a single bond and each $R^{1'}$ is independently hydrogen, an amino acid side chain, an alkyl, an alkenyl, an alkynyl, a cycloalkyl, a heterocyclyl, an aryl, a heteroaryl, or an arylalkyl;
- each $R^1$ is independently hydrogen, an amino acid side chain, an alkyl, an alkenyl, an alkynyl, a cycloalkyl, a heterocyclyl, an aryl, a heteroaryl, or an arylalkyl; and wherein:
- (a) at least one $R^1$ at the positions labeled "Glu" is a glutamic acid side chain,
- (b) at least one $R^1$ at the positions labeled "Leu" is a leucine side chain, (c) at least one $R^1$ at the positions labeled "Ala" is an alanine side chain,
(d) at least one $R^1$ at the positions labeled "Arg" is an arginine side chain,
(e) at least one $R^1$ at the positions labeled "Asp" is an aspartic acid side chain, and
(f) at least one $R^1$ at the positions labeled "Gln" is a glutamine side chain;

$R^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

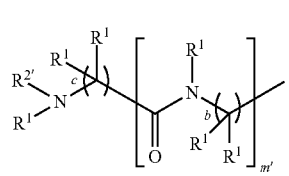

A $R^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

$R^3$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

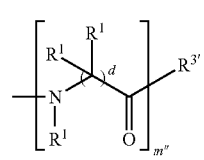

B $R^{3'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —$N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

each $R^4$ is independently hydrogen, an alkyl, an alkenyl, an alkynyl, a cycloalkyl, a heterocyclyl, an aryl, a heteroaryl, or an arylalkyl;

$R^{4'}$ is hydrogen, an alkyl, an alkenyl, an alkynyl, a cycloalkyl, a heterocyclyl, an aryl, a heteroaryl, an arylalkyl, or a double bond between $C(R^{4'},R^4)$ and B;

a is one or two;
each b is independently one or two;
c is one or two;
each d is independently one or two;
m' is zero or any number;
m" is zero or any number;
n' and n" are each independently zero, one, two, three, or four;
each o is independently one or two; and
p is one or two;

(ii) a compound of Formula IIa, IIb, IIc, IId, or, IIe:

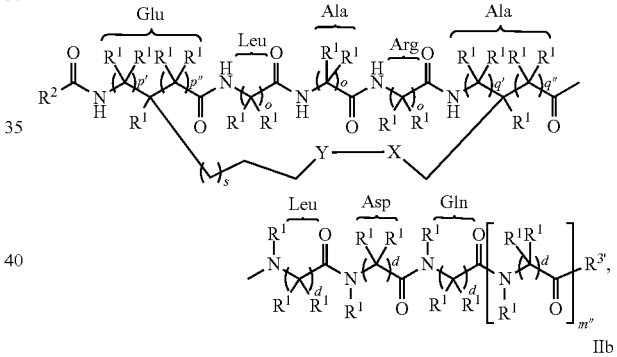

IIa

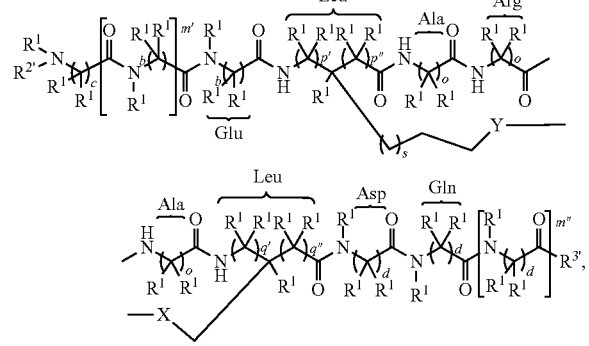

IIb

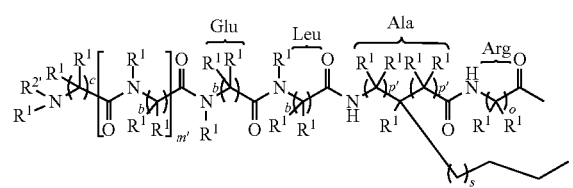

IIc

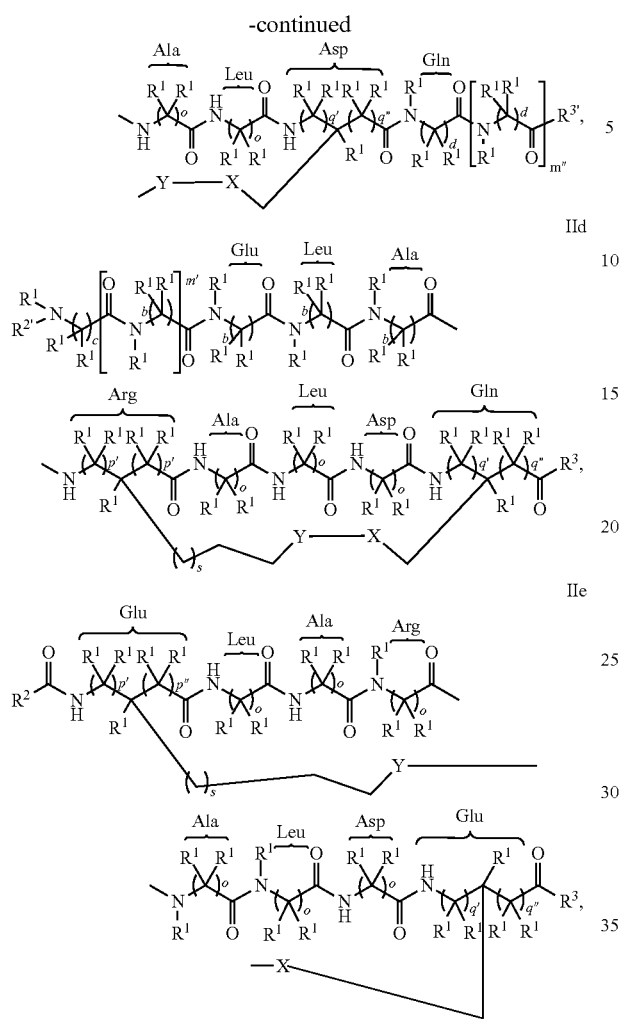

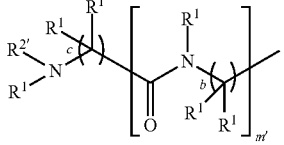

wherein:
  each $R^1$ is independently hydrogen, an amino acid side chain, an alkyl, an alkenyl, an alkynyl, a cycloalkyl, a heterocyclyl, an aryl, a heteroaryl, or an arylalkyl; and
  wherein:
  (a) at least one $R^1$ at the positions labeled "Glu" is a glutamic acid side chain,
  (b) at least one $R^1$ at the positions labeled "Leu" is a leucine side chain,
  (c) at least one $R^1$ at the positions labeled "Ala" is an alanine side chain,
  (d) at least one $R^1$ at the positions labeled "Arg" is an arginine side chain,
  (e) at least one $R^1$ at the positions labeled "Asp" is an aspartic acid side chain, and
  (f) at least one $R^1$ at the positions labeled "Gln" is a glutamine side chain;
  $R^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; $-OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; $-(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

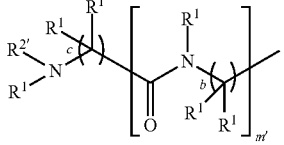

$R^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; $-OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or $-(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
  $R^3$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; $-OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; $-N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

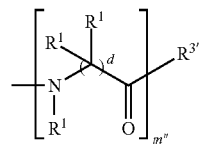

$R^{3'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; $-OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or $-N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
  each b is independently one or two;
  c is one or two;
  each d is independently one or two;
  m' is zero or any number;
  m" is zero or any number;
  each o is independently one or two;
  one of p' and p" is zero and the other is zero or one;
  one of q' and q" is zero and the other is zero or one;

s is one, two, three, four, or five; and

Y—X is a hydrocarbon, an amide bond, an alkane, an alkene, an alkyne, a triazole, or a disulfide bond; and (iii) a compound of Formula IIIa:

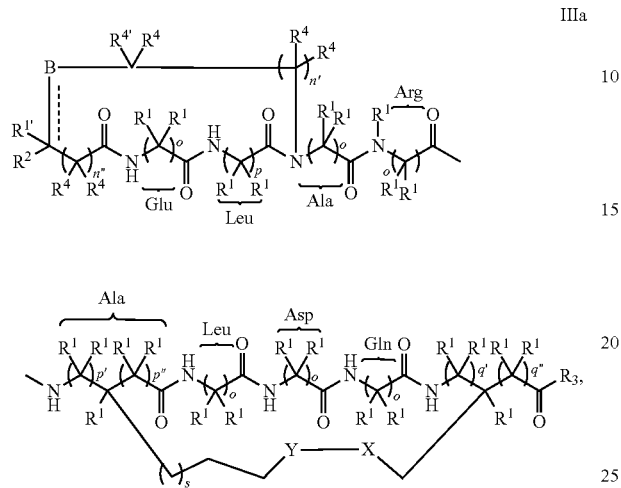

IIIa wherein:

B is $C(R^1)(R^{1'})$, O, S, or $NR^1$;

------ is a double bond and each $R^{1'}$ is absent; or

------ is a single bond and each $R^{1'}$ is independently hydrogen, an amino acid side chain, an alkyl, an alkenyl, an alkynyl, a cycloalkyl, a heterocyclyl, an aryl, a heteroaryl, or an arylalkyl;

each $R^1$ is independently hydrogen, an amino acid side chain, an alkyl, an alkenyl, an alkynyl, a cycloalkyl, a heterocyclyl, an aryl, a heteroaryl, or an arylalkyl; and wherein:

(a) at least one $R^1$ at the positions labeled "Glu" is a glutamic acid side chain, (b) at least one $R^1$ at the positions labeled "Leu" is a leucine side chain, (c) at least one $R^1$ at the positions labeled "Ala" is an alanine side chain, (d) at least one $R^1$ at the positions labeled "Arg" is an arginine side chain, (e) at least one $R^1$ at the positions labeled "Asp" is an aspartic acid side chain, and (f) at least one $R^1$ at the positions labeled "Gln" is a glutamine side chain;

$R^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

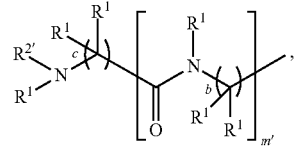

A wherein:

$R^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

m' is zero or any number;

each b is independently one or two; and c is one or two;

$R^3$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

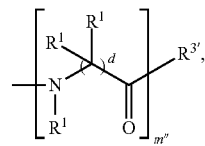

B wherein:

$R^{3'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —$N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

m" is zero or any number; and each d is independently one or two;

each $R^4$ is independently hydrogen, an alkyl, an alkenyl, an alkynyl, a cycloalkyl, a heterocyclyl, an aryl, a heteroaryl, or an arylalkyl;

$R^{4'}$ is hydrogen, an alkyl, an alkenyl, an alkynyl, a cycloalkyl, a heterocyclyl, an aryl, a heteroaryl, an arylalkyl, or a double bond between $C(R^{4'},R^4)$ and B;

n' and n" are each independently zero, one, two, three, or four;

each o is independently one or two;

p is one or two;

one of p' and p" is zero and the other is zero or one;

one of q' and q" is zero and the other is zero or one;

s is one, two, three, four, or five; and

Y—X is a hydrocarbon, an amide bond, an alkane, an alkene, an alkyne, a triazole, or a disulfide bond.

2. The peptidomimetic according to claim 1, wherein B is $C(R^1)(R^{1'})$.

3. The peptidomimetic according to claim 1, wherein B is O.

4. The peptidomimetic according to claim 1, wherein B is S.

5. The peptidomimetic according to claim 1, wherein B is $NR^1$.

6. The peptidomimetic according to claim 1, wherein 9 to 12 atoms form the backbone of the macrocycle portion of the compound.

7. The peptidomimetic according to claim 1, wherein 12 to 15 atoms form the backbone of the macrocycle portion of the compound.

8. The peptidomimetic according to claim 1, wherein 15 to 18 atoms form the backbone of the macrocycle portion of the compound.

9. The peptidomimetic according to claim 1, wherein 20 to 24 atoms form the backbone of the macrocycle portion of the compound.

10. The peptidomimetic according to claim 1, wherein the peptidomimetic is a compound of Formula IIa, and $R^2$ is hydrogen, an alkyl, an alkenyl, an alkynyl, a cycloalkyl, a heterocyclyl, an aryl, a heteroaryl, or an arylalkyl.

11. A pharmaceutical composition comprising a peptidomimetic according to claim 1 and a pharmaceutically acceptable vehicle.

12. The pharmaceutical composition according to claim 11, wherein the peptidomimetic is a compound of Formula Ia, IIa, or IIIa.

* * * * *